US010550400B2

(12) United States Patent
Navarro et al.

(10) Patent No.: US 10,550,400 B2
(45) Date of Patent: Feb. 4, 2020

(54) METHODS TO MONITOR POST-TRANSLATIONAL GENE SILENCING ACTIVITY IN PLANT TISSUES/CELL TYPES RELEVANT FOR PATHOGEN ENTRY, PROPAGATION OR REPLICATION

(71) Applicants: Paris Sciences et Lettres—Quartier Latin, Paris (FR); Institut National de la Sante et de la Recherche Medicale (INSERM), Paris (FR); Centre National de la Recherche Scientifique (CNRS), Paris (FR)

(72) Inventors: Lionel Navarro, Antony (FR); Odon Thiebeauld, Bourg la Reine (FR)

(73) Assignees: Paris Sciences et Lettres—Quartier Latin, Paris (FR); Institut National de la Sante et de la Recherche Medicale (INSERM), Paris (FR); Centre National de la Recherche Scientifique (CNRS), Paris (FR)

( * ) Notice: Subject to any disclaimer, the term of this patent is extended or adjusted under 35 U.S.C. 154(b) by 71 days.

(21) Appl. No.: 15/536,191

(22) PCT Filed: Dec. 15, 2015

(86) PCT No.: PCT/EP2015/079893
§ 371 (c)(1),
(2) Date: Jun. 15, 2017

(87) PCT Pub. No.: WO2016/096923
PCT Pub. Date: Jun. 23, 2016

(65) Prior Publication Data
US 2017/0349907 A1    Dec. 7, 2017

(30) Foreign Application Priority Data
Dec. 15, 2014   (EP) .................... 14307040

(51) Int. Cl.
*C12N 15/82* (2006.01)
*C12N 15/113* (2010.01)
*C12N 15/65* (2006.01)

(52) U.S. Cl.
CPC ........ *C12N 15/8209* (2013.01); *C12N 15/113* (2013.01); *C12N 15/65* (2013.01); *C12N 15/8216* (2013.01); *C12N 15/8241* (2013.01); *C12N 15/8279* (2013.01)

(58) Field of Classification Search
CPC ................................ C12N 15/8209
USPC ....................................... 435/419
See application file for complete search history.

(56) References Cited

U.S. PATENT DOCUMENTS 6,452,067 B1    9/2002   Bedbrook et al.
2010/0125919 A1*   5/2010   Navarro ............... C12N 15/111
                                                                    800/13

FOREIGN PATENT DOCUMENTS

WO    2008/087562 A2    7/2008

OTHER PUBLICATIONS

Dunoyer et al. 2005, Nature Genetics 37:1356-1360.*
Bechtold, N. et al., In planta Agrobacterium mediated gene transfer by infiltration of adult *Arabidopsis thaliana* plants. C. R. Acad. Sci. Paris, Life Sciences, 1993, vol. 316, pp. 1194-1199.
Bologna, N.G. et al., (2014) The diversity, biogenesis, and activities of endogenous silencing small RNAs in *Arabidopsis*. Annu Rev Plant Biol., 2014, vol. 65, pp. 473-503.
Boller, T. et al., A renaissance of elicitors: perception of microbe-associated molecular patterns and danger signals by pattern-recognition receptors, Annu Rev Plant Biol., 2009, vol. 60, pp. 379-406.
Brodersen, P. et al., Widespread translational inhibition by plant miRNAs and siRNAs. Science. 2008, vol. 320 (5880), pp. 1185-1190.
Chen, X. et al., HEN1 functions pleiotropically in *Arabidopsis* development and acts in C function in the flower, Development, 2002, vol. 129, pp. 1085-1094.
Dalmay, T. et al., An RNA-dependent RNA polymerase gene in *Arabidopsis* is required for posttranscriptional gene silencing mediated by a transgene but not by a virus, Cell, 2000, vol. 101, pp. 543-553.
Deleris, A. et al., Hierarchical action and inhibition of plant Dicer-like proteins in antiviral defense, Science, 2006, vol. 313, pp. 68-71.
Diaz-Pendon, J.A. et al., Suppression of antiviral silencing by cucumber mosaic virus 2b protein in *Arabidopsis* is associated with drastically reduced accumulation of three classes of viral small interfering RNAs, Plant Cell, 2007, 19(6), pp. 2053-2063.

(Continued)

*Primary Examiner* — Li Zheng
(74) *Attorney, Agent, or Firm* — Banner & Witcoff, Ltd.

(57) ABSTRACT

The invention relates to transgenic plants comprising an inverted-repeat construct which triggers post-transcriptional gene silencing of an endogenous visual reporter gene driven by a tissue-specific promoter wherein said tissue is relevant for pathogen entry, propagation or replication and their uses for screening natural or synthetic molecules, microorganisms or extracts from micro- or macro-organisms for their potential ability to inhibit pathogen entry, propagation or replication in plants by enhancing PTGS or for characterizing the mode of action of natural or synthetic molecules that are known to enhance plant disease resistance through an ill-defined mode of action.

5 Claims, 6 Drawing Sheets
Specification includes a Sequence Listing.

(56) References Cited

OTHER PUBLICATIONS

DeWitt, N.D. et al., Evidence for a plasma membrane proton pump in phloem cells of higher plants, The Plant Journal, 1991, 1(1), pp. 121-128.
Dou, D. et al. Phytopathogen effectors subverting host immunity: different foes, similar battleground, Cell Host & Microbe, 2012, vol. 12, pp. 484-495.
Ellendorff, U. et al., RNA silencing is required for Arabidopsis defence against Verticillium wilt disease, Journal of Experimental Botany, 2009, vol. 60, No. 2, pp. 591-602.
Fahlgren, N. et al., High-throughput sequencing of Arabidopsis microRNAs: evidence for frequent birth and death of MIRNA genes, PLoS One, 2007, Issue 2, pp. 1-14.
Frerigmann, H. et al., Glucosinolates are produced in trichomes of Arabidopsis thaliana, Frontiers in Plant Science, 2012, vol. 3, Article 242, pp. 1-13.
Fu, Z.Q. et al., A type III effector ADP-ribosylates RNA-binding proteins and quells plant immunity, Nature, May 2007, vol. 447, pp. 284-288.
Gardiner, J.C. et al., Control of cellulose synthase complex localization in developing xylem, The Plant Cell, 2003, vol. 15, pp. 1740-1748.
Hamilton, A.J. et al., A species of small antisense RNA in post-transcriptional gene silencing in plants, Science, 1999, vol. 286, pp. 950-952.
Hirakawa, Y. et al. TDIF peptide signaling regulates vascular stem cell proliferation via the WOX4 homeobox gene in Arabidopsis, The Plant Cell, 2010, vol. 22, pp. 2618-2629.
Horbach, R. et al., When and how to kill a plant cell: infection strategies of plant pathogenic fungi, Journal of Plant Physiology, 2011, vol. 168, pp. 51-62.
Hugouvieux, V. et al., Entry of Xanthomonas campestris pv. campestris into hydathodes of Arabidopsis thaliana leaves: a system for studying early infection events in bacterial pathogenesis, Molecular Plant-Microbe Interactactions, 1998, vol. 11, No. 6, pp. 537-543.
Jakoby, M.J. et al., Transcriptional profiling of mature Arabidopsis trichomes reveals that NOECK encodes the MIXTA-like transcriptional regulator MYB106, Plant Physiology, 2008, vol. 148, pp. 1583-1602.
Ji, L. et al., Regulation of small RNA stability: methylation and beyond, Cell Research, 2012, vol. 22, No. 4, pp. 624-636.
Jones, J.D. et al., The plant immune system, Nature, 2006, vol. 444, pp. 323-329.
Karimi ,M. et al., GATEWAY vectors for Agrobacterium-mediated plant transformation, Trends in Plant Science, 2002, vol. 7, No. 5, pp. 193-195.
Li, J. J et al., Methylation protects miRNAs and siRNAs from a 3'-end uridylation activity in Arabidopsis, Current Biology, 2005, vol. 15, pp. 1501-1507.
Li, Y. et al., Identification of microRNAs involved in pathogen-associated molecular pattern-triggered plant innate immunity, Plant Physiology, 2010, vol. 152, pp. 2222-2231.
Melotto, M. et al., Plant stomata function in innate immunity against bacterial invasion, Cell, 2006, vol. 126, pp. 969-980.
Mendgen, K. et al., Plant infection and the establishment of fungal biotrophy, Trends in Plant Science, 2002, 7 (8):352-356.
Mourrain, P. et al, Arabidopsis SGS2 and SGS3 genes are required for postranscriptional gene silencing and Natural Virus Resistance, Cell, 2000, vol. 101, pp. 533-542.
Navarro, L,. et al., A plant miRNA contributes to antibacterial resistance by repressing auxin signaling, Science, 2006, vol. 312, pp. 436-439.
Navarro, L. et al., Suppression of the microRNA pathway by bacterial effector proteins, Science, 2008, vol. 321, pp. 964-967.
Nikovics, K. et al., The balance between the MIR164A and CUC2 genes controls leaf margin serration in Arabidopsis, The Plant Cell, 2006, vol. 18, pp. 2929-2945.
Okumoto, S. et al., High affinity amino acid transporters specifically expressed in xylem parenchyma and developing seeds of Arabidopsis, The Journal of Biological Chemistry, 2002, vol. 277, pp. 45338-45346.
Pumplin, N. et al., RNA silencing suppression by plant pathogens: defence, counter-defence and counter-counter-defence, Nature Reviews Microbiology, 2013, vol. 11, pp. 745-760.
Qiao, Y. et al., Oomycete pathogens encode RNA silencing suppressors, Nature Genetics, 2013, vol. 45, No. 3, pp. 330-333.
Qu, F. et al., Arabidopsis DRB4, AGO1, AGO7, and RDR6 participate in a DCL4-initiated antiviral RNA silencing pathway negatively regulated by DCL1, Proc Natl Acad Sci., 2008, vol. 105, No. 38, pp. 14732-14737.
Schwach, F. et al., An RNA-dependent RNA polymerase prevents meristem invasion by potato virus X and is required for the activity but not the production of a systemic silencing signal, Plant Physiology, 2005, vol. 138, pp. 1842-1852.
Smith, L.M., An SNF2 protein associated with nuclear RNA silencing and the spread of a silencing signal between cells in Arabidopsis, The Plant Cell, 2007, vol. 19, pp. 1507-1521.
Susek R. E. et al., Signal transduction mutants of Arabidopsis uncouple nuclear CAB and RBCS gene expression from chloroplast development, Cell, 1993, vol. 74, pp. 787-799.
Thomma, B.P. et al., Cladosporium fulvum (syn. Passalora fulva), a highly specialized plant pathogen as a model for functional studies on plant pathogenic Mycosphaerellaceae, Molecular Plant Pathology, 2005, vol. 6, No. 4, pp. 379-393.
Xie, Z. et al., Genetic and functional diversification of small RNA pathways in plants, PLoS Biology, 2004 , vol. 2, Issue 5, pp. 0642-0652.
Xie, Z. et al., DICER-LIKE 4 functions in trans-acting small interfering RNA biogenesis and vegetative phase change in Arabidopsis thaliana, Proc Natl Acad Sci., 2005, vol. 102, No. 35, pp. 12984-12989.
Xin, X.F. et al., Pseudomonas syringae pv. tomato DC3000: a model pathogen for probing disease susceptibility and hormone signaling in plants, Annu Rev Phytopathol., 2013, vol. 51, pp. 473-498.
Yang, Y. et al., Isolation of a strong Arabidopsis guard cell promoter and its potential as a research tool, Plant Methods, 2008, vol. 4, No. 6, pp. 1-15.
Yu, A. et al., Dynamics and biological relevance of DNA demethylation in Arabidopsis antibacterial defense, Proc Natl Acad Sci., 2013, vol. 110, No. 6, pp. 2389-2394.
Yu, B. et al., Methylation as a crucial step in plant microRNA biogenesis, Science, 2005, vol. 307, pp. 932-935.
Weiberg, A. et al., Small RNAs: A New Paradigm in Plant-Microbe Interactions. Annu. Rev. Phytopathol., 2014, vol. 52, pp. 495-516.
Zhao, H. et al., A single amino acid substitution in IIIf subfamily of basic helix-loop-helix transcription factor AtMYC1 leads to trichome and root hair patterning defects by abolishing its interaction with partner proteins in Arabidopsis, Journal of Biological Chemistry, 2012, vol. 287, No. 17, pp. 14109-14121.
Dunoyer, P. et al, DICER-LIKE 4 is required for RNA interference and produces the 21-nucleotide small interfering RNA component of the plant cell-to-cell silencing signal, Nature Genetics, Dec. 2005, vol. 37, No. 12, pp. 1356-1360.
Felippes, F. F. D. et al, Comparative analysis of non-autonomous effects of tasiRNAs and miRNAs in Arabidopsis thaliana, Nucleic Acids Research, 2011, vol. 39, No. 7, pp. 2880-2889.
Orzaez, D. et al, A Visual Reporter System for Virus-Induced Gene Silencing in Tomato Fruit Based on Anthocyanin Accumulation, Plant Physiology, Jul. 2009, vol. 150, No. 3, pp. 1122-1134.
Johansen, W. et al, Viral suppressor proteins show varying abilities and effectiveness to suppress transgene-induced post-transcriptional gene silencing of endogenous Chalcone synthase in transgenic Arabidopsis, Plant Cell Reports, 2008, vol. 27, No. 5, pp. 911-921.

\* cited by examiner

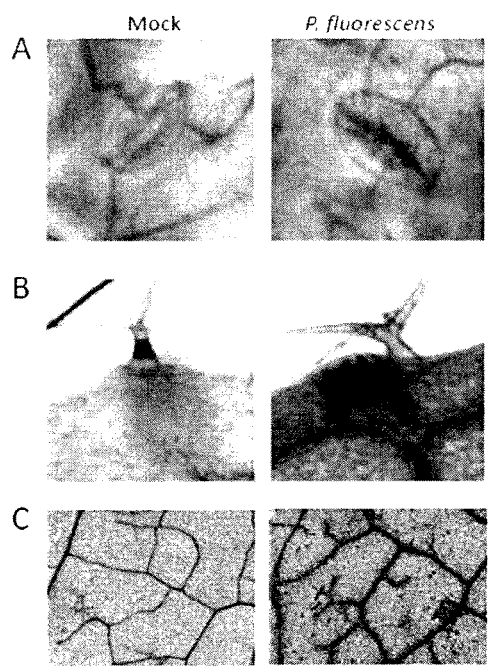
Figure 1. Hydrogen peroxide is mainly produced upon bacterial recognition in stomata, hydathodes and in leaf vasculature.

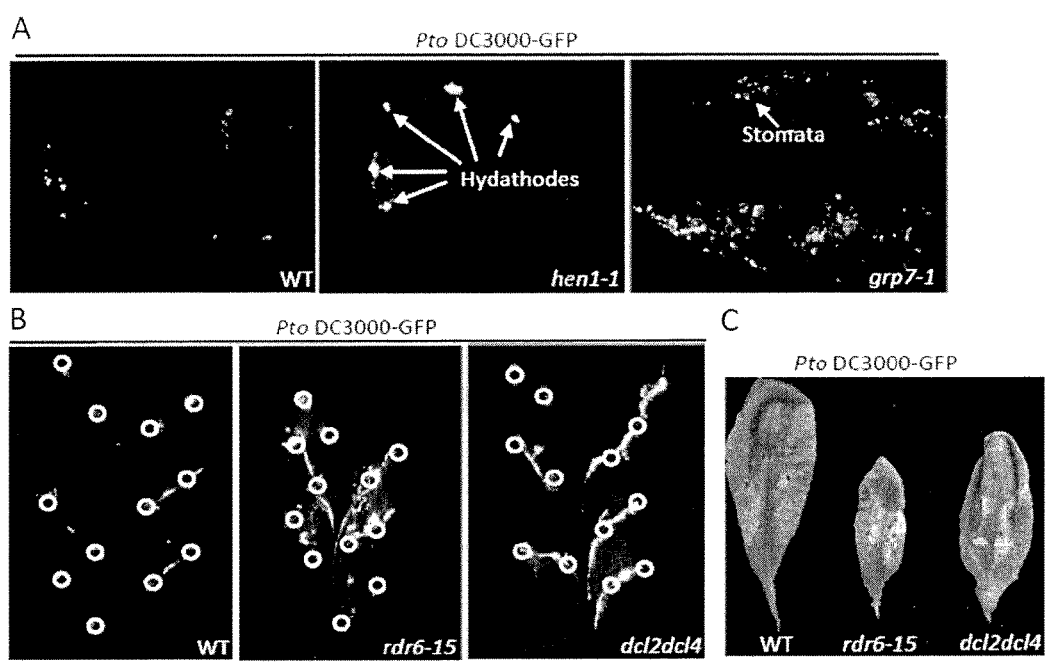
Figure 2. PTGS-deficient mutants are compromised in bacterial entry and propagation.

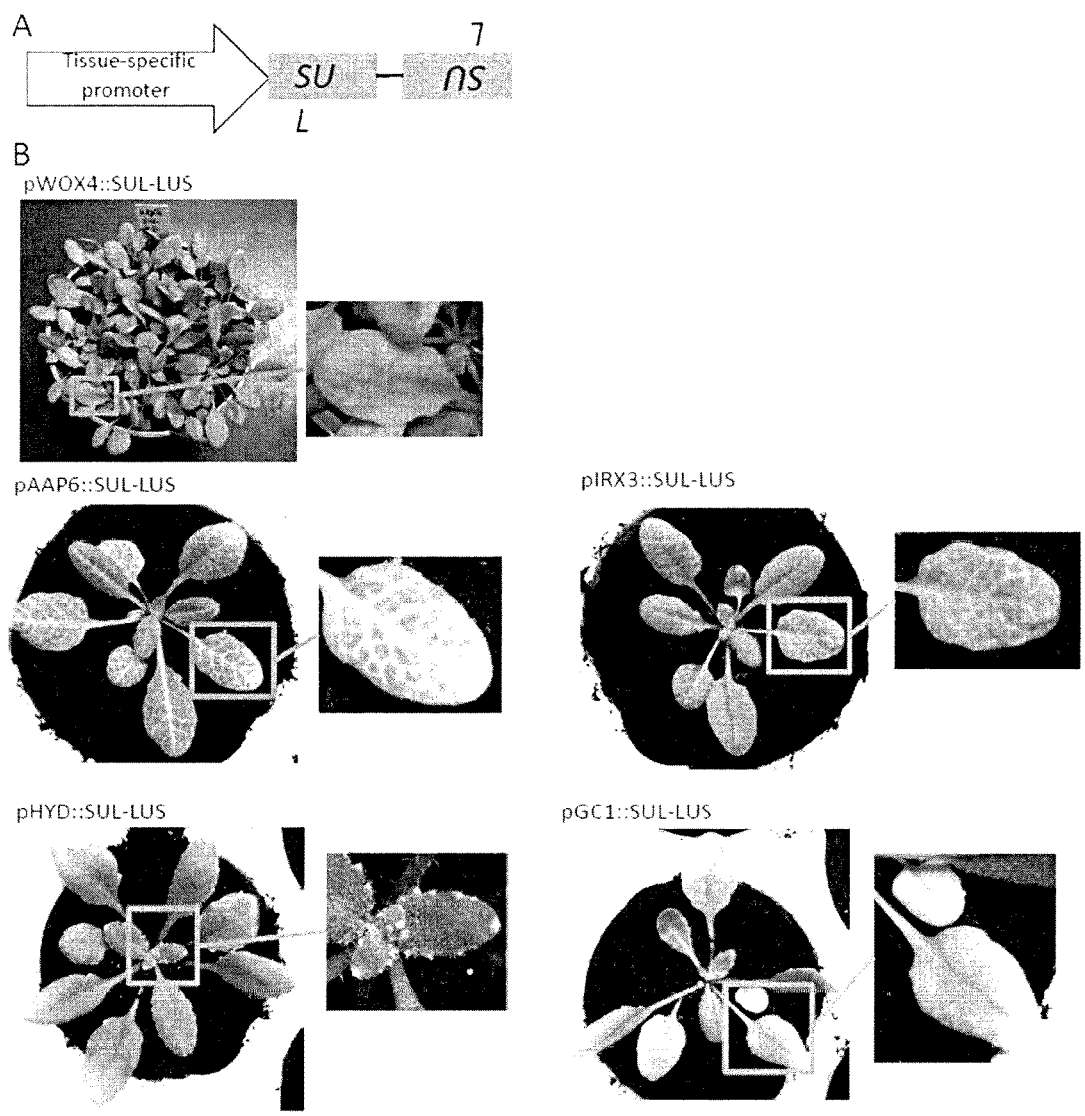
Figure 3. Arabidopsis tissue-specific sensors of Inverted Repeat Post Transcriptional Gene Silencing (IR-PTGS).

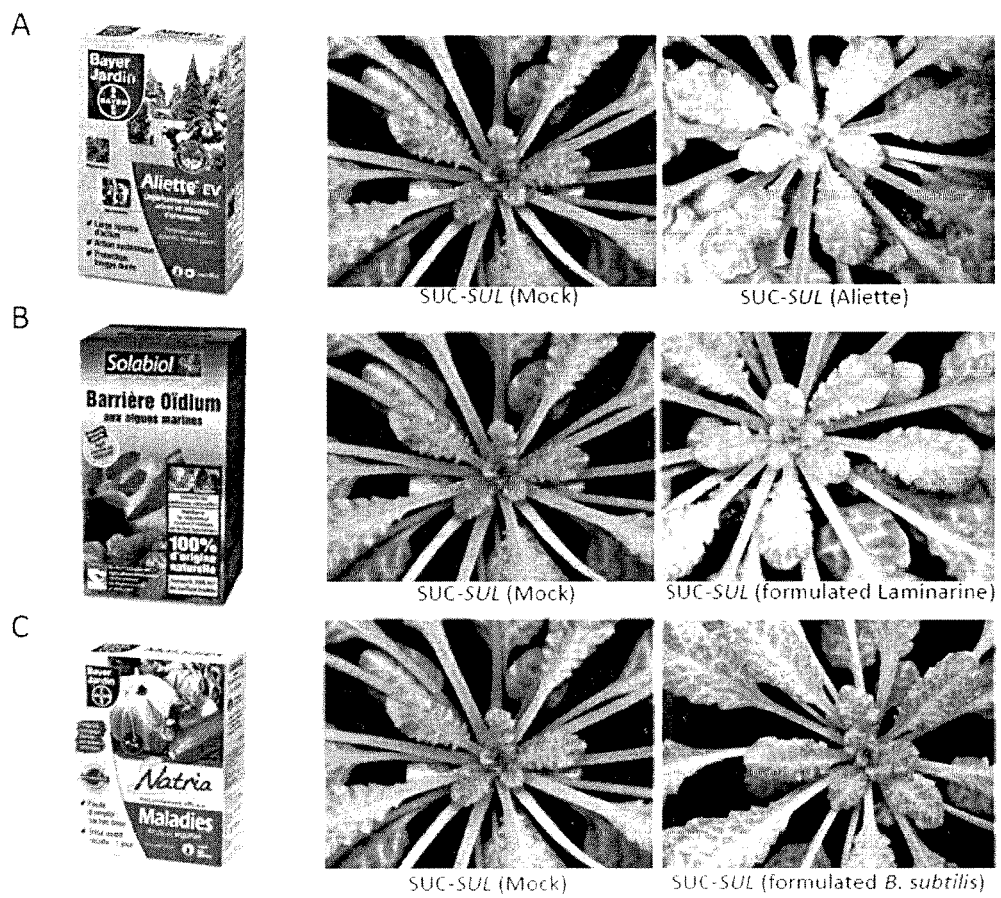
Figure 4. Formulated Fosetyl-Al and laminarine compounds (A and B) but not formulated *Bacillus subtilis* (C) enhance IR-PTGS.

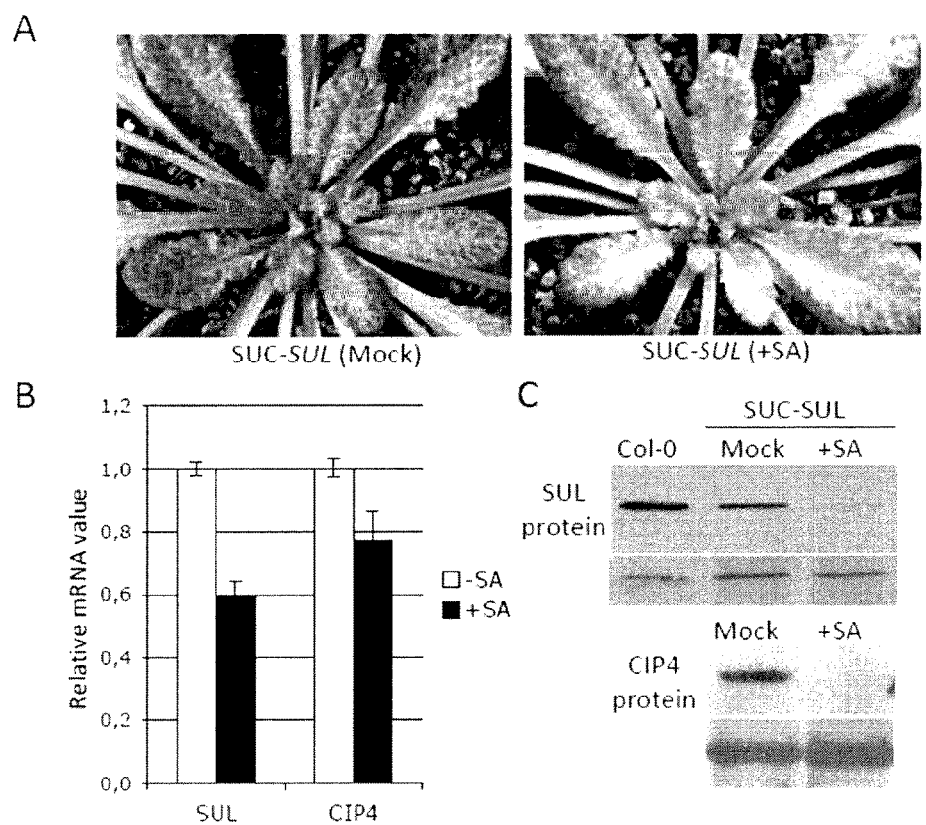
Figure 5. Salicylic acid (SA) promotes IR-PTGS.

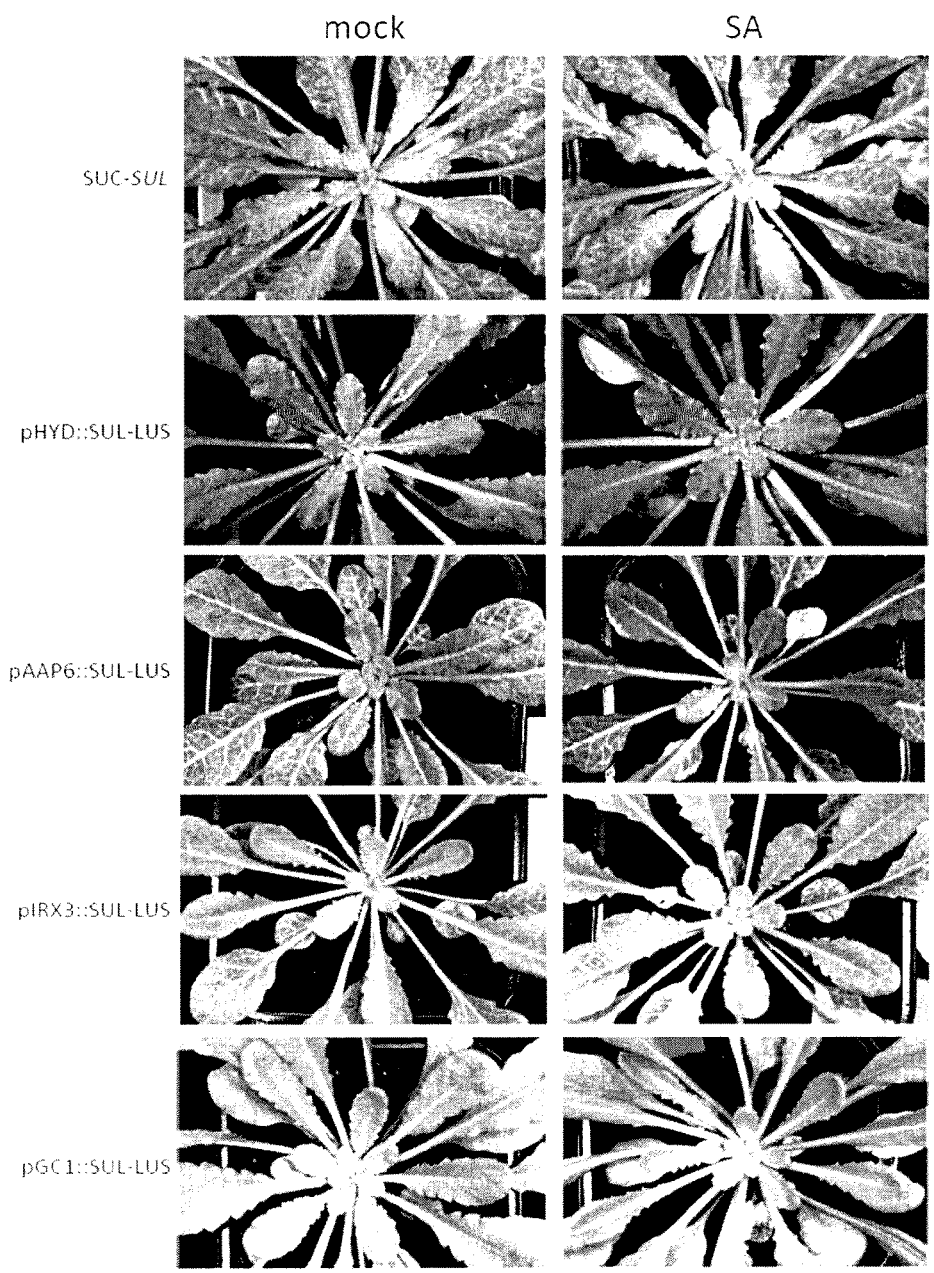
Figure 6 Salicylic acid (SA) promotes IR-PTGS within and around phloem companion cells but not in hydathodes, xylem parenchyma cells or guard cells.

METHODS TO MONITOR POST-TRANSLATIONAL GENE SILENCING ACTIVITY IN PLANT TISSUES/CELL TYPES RELEVANT FOR PATHOGEN ENTRY, PROPAGATION OR REPLICATION

RELATED APPLICATIONS

This application is a National Stage Application under 35 U.S.C. 371 of co-pending PCT application PCT/EP2015/079893 designating the United States and filed Dec. 15, 2015; which claims the benefit of EP application number 14307040.7 and filed Dec. 15, 2014 each of which are hereby incorporated by reference in their entireties.

The present invention pertains to the field of agriculture. The invention relates to a method to monitor post-transcriptional gene silencing (PTGS) activity triggered by inverted-repeat in plant tissues/cell types that are relevant for the entry, propagation or replication of phytopathogens. These reporter systems can for instance be used to characterize the modes of action of known natural/synthetic compounds, microorganisms or extracts from micro- or macro-organisms that are known to promote disease resistance in crops. In addition, these reporter lines can be used to identify novel natural/synthetic compounds, microorganisms or extracts from micro- or macro-organisms that can promote PTGS and likely increase disease resistance in various cultivated plants.

BACKGROUND AND STATE OF THE ART

The innate immune response is the first line of defense against pathogens, and plays a critical role in antimicrobial defence. This response is initiated by host-encoded Pattern-Recognition Receptors (PRRs) that recognize evolutionarily conserved pathogen-derived signatures, known as Microbe-Associated Molecular Patterns (MAMPs), and activate MAMP-triggered immunity (MTI) (Boller & Felix, 2009). Furthermore, plants have evolved another strategy to perceive microbial pathogens through disease resistance (R) proteins, which recognize, directly or indirectly, divergent pathogen virulence determinants known as effector proteins, and establish effector-triggered immunity (ETI) (Jones & Dangl, 2006). Upon detection of MAMPs or pathogen effectors, plant cells rapidly induce a series of signalling events that involve for instance, the differential expression of short interfering RNAs (siRNAs) and microRNAs (miR-NAs) (Pumplin N & Voinnet O, 2013). Recently, several siRNAs and miRNAs were found to orchestrate MTI and ETI responses (Weiberg et al., 2014), implying a key role of RNA silencing in the regulation of the plant immune system.

RNA silencing is an ancestral gene regulatory mechanism that controls gene expression at the transcriptional (TGS, Transcriptional Gene Silencing) and post-transcriptional (PTGS, Post-transcriptional Gene Silencing) levels. In plants, this mechanism has been initially characterized in antiviral resistance (Hamilton & Baulcombe, 1999). The core mechanism of RNA silencing starts with the production of double stranded RNAs (dsRNAs) that are processed by RNase-III enzymes DICERs into 20-24 nt small RNA duplexes that subsequently associate with an Argonaute (AGO) protein, which represent the central component of the RNA-induced silencing complexes (RISC). One strand, the guide, remains bound to the AGO effector protein to regulate genes in a mature RISC, while the other strand, the passenger, is degraded. The plant model *Arabidopsis thaliana* encodes 4 DICER-like proteins and 10 AGOs. DCL1 processes miRNA precursors into miRNA/miRNA* duplexes and the guide miRNA strand directs AGO1-RISC to sequence complementary mRNA targets to trigger their degradation and/or translation inhibition. DCL2 and DCL4 are involved in the biogenesis of short interfering RNAs (siRNAs) derived from viral dsRNAs and play a critical role in antiviral resistance (Deleris et al., 2006; Diaz-Pendon et al., 2007). These DICER-like proteins are also involved, together with DCL3, in the production of siRNAs derived from transposable elements, read through, convergent or overlapping transcription, endogenous hairpins as well as some miRNA precursors (Bologna & Voinnet, 2014). In addition, a large proportion of dsRNAs are produced by RNA-dependent RNA polymerases (RDRs) that convert single stranded RNAs into dsRNAs. RDR6, which is one out of six *Arabidopsis* RDRs, produces dsRNAs from viral, transgene transcripts as well as some endogenous transcripts including transposable elements (Mourrain et al., 2000; Dalmay et al, 2000.; Schwach et al., 2005; Xie et al., 2004). These dsRNAs are processed in part by DCL4 and DCL2 into 21 nt and 22 nt siRNAs, respectively, which direct PTGS of endogenous sequence complementary mRNA targets or exogenous RNAs derived from sense-transgenes or viral RNAs (Bologna & Voinnet, 2014). Furthermore, both siRNA and miRNA duplexes are methylated by the small RNA methyltransferase HEN1 and this modification is essential for their stability (Yu et al, 2005; Li et al., 2005; Chen et al., 2012).

Although endogenous miRNAs and siRNAs were initially characterized in various plant development processes, they have more recently emerged as key regulators of the plant innate immune response (Pumplin & Voinnet, 2013). For instance, the miR393 is a conserved microRNA that is induced during MTI and that contributes to antibacterial resistance in *Arabidopsis* (Navarro et al., 2006, 2008; Fahlgren et al., 2007; Li et al., 2010). Furthermore, phenotypical analyses in mutants that are defective in PTGS exhibit enhanced disease susceptibility to fungal, bacterial and oomycete pathogens (Navarro et al., 2008; Qiao et al., 2013; Ellendorff U et al., 2009; Navarro & Voinnet, 2008 WO/2008/087562), supporting a central role of this gene regulatory process in resistance against unrelated pathogens. However, despite the well-established role of RNA silencing in resistance against viral and non-viral pathogens, very little is known on the physiological relevance, or on the activity, of RNA silencing in tissues that are relevant for the entry and/or propagation of phytopathogens.

Phytopathogenic microbes can be divided into biotrophs, hemibiotrophs and necrotrophs according to their different lifestyles. Biotrophic pathogens can take-up nutrients from living host cells and maintain host cell viability, while necrotrophs kill host cells and feed on dead tissues. Hemibiotrophs use an early biotrophic phase followed by a necrotrophic phase. These phytopathogenic microbes use different strategies to enter inside host tissues. The majority of fungal and oomycete pathogens first produce spores, which adhere to the plant surface and further germinate to form a germ tube. Subsequently, the germ tube develops an appressorium that can perforate, through a penetration peg, the cuticle and cell wall layer through mechanical forces (Horbach et al., 2011) and therefore enter inside host tissues. Once inside plant tissues, the hyphal tip forms a second specialized structure referred to as the haustorium that can uptake nutrients from host cells but also represents a major site of pathogen effector secretion (Mendgen & Hahn, 2002; Horbach et al., 2011). Other pathogens do not perforate the cuticle cell wall layer but instead use natural openings to reach internal host tissues. For instance, hemibiotrophic bacterial pathogens such as *Pseudomonas* and *Xanthomonas* use hydathodes, stomata or woundings as natural entry sites for their endophytic colonization (Dou & Zhou, 2012). These bacterial pathogens can also enter plant tissues through the base of trichomes in some instances (Xin & He, 2013). Some fungal pathogens can also use natural openings to enter plant tissues. For example, *Cladosporium fulvum* colonizes internal host tissues through stomatal openings by forming long, branched intercellular hyphal structures with no obvious haustorium (Thomma et al., 2005). It is therefore not surprising that plants have evolved sensitive pathogen recognition mechanisms, and sophisticated defense responses, in these tissues/cell types to prevent pathogen entry (Melotto et al., 2006; Hugouvieux et al., 1998). As an example, plants can perceive bacterial MAMPs at the level of guard cells and in turn trigger stomatal closure, which efficiently controls the access of bacterial pathogens to internal host tissues (Melotto et al., 2006). Active defense responses have also been reported at hydathodes and at the base of trichomes (Hugouvieux et al., 1998; Yu et al., 2013; Frerigmann et al., 2012; Jakoby et al., 2008), although very little is known on the detailed mechanisms that orchestrate such local innate immune responses.

Once inside the intercellular space of plant leaves, biotrophic and hemibiotrophic pathogens use different strategies to colonize distal plant tissues. For example, RNA viruses use alive phloem tissues as a major route to propagate in systemic tissues and this viral spreading is restricted by PTGS. As an example, *Arabidopsis* mutants that are defective in the two major antiviral Dicer-like 2 (DCL2) and DCL4 exhibit long distance propagation of several RNA viruses (Deleris et al., 2006; Diaz-Pendon et al., 2007). By contrast, fungal, oomycete and bacterial pathogens can spread in distal plant tissues through xylem vessels, which are dead cells that transport nutrients and water from the root to the aerial part of the plant. The plant defense responses that restrict vascular spreading involve multiple processes including, for instance, the production of reactive oxygen species (ROS) and antimicrobial proteins from adjacent xylem parenchyma cells, the plant-induced physical obstruction of vascular vessels through lignification, the efficient recognition of pathogen effectors through R proteins (Guy et al., 2013). However, it is not known whether PTGS plays any role in restricting the propagation of such non-viral pathogens within and around xylem vessels.

In the present invention, the inventors first provide experimental evidence that PTGS plays a critical role in controlling the entry of a virulent *Pseudomonas syringae* strain at the level of hydathodes and stomata in *Arabidopsis thaliana*. Furthermore, they show that PTGS efficiently restricts vascular propagation of this pathogenic bacterium in *Arabidopsis* leaf vasculature. Based on these observations, they have selected the most relevant promoters that are active enough in dedicated tissues or cell types to generate a whole series of visual inverted repeat PTGS reporter lines in the model plant *Arabidopsis thaliana*. These PTGS reporter lines are based on the tissue-specific silencing of an endogenous gene involved in chlorophyll biosynthesis and therefore allow an easy monitoring of PTGS activity in tissues/cell types that are relevant for pathogen entry, propagation or replication, namely the hydathodes, guard cells, epidermal cells, xylem parenchyma cells, cells at the base of trichomes, phloem companion cells and mesophyll cells.

The intended applications therefore deal with methods to increase disease resistance in cultivated plants by enhancing PTGS activity in tissues/cell types that are relevant for pathogen entry, propagation or replication. For instance, they can be used for high-throughput screening of natural or synthetic compounds that can enhance the chlorotic phenotype and likewise promote PTGS in tissues/cell types that are physiologically relevant for plant disease management. Given the critical and widespread role of PTGS in plant disease resistance, the identified PTGS inducer compounds will likely enhance resistance against unrelated pathogens in *Arabidopsis* but also in agriculturally important crops by preventing pathogen entry, propagation and/or replication. As a proof-of-concept experiment, the inventors have challenged these PTGS sensors with commercially available natural or synthetic—active or formulated—compounds that are known to increase disease resistance in cultivated plants. Results from these analyses indicated that well-characterized compounds can indeed promote PTGS on one specific silencing reporter. Besides providing novel insights into the mode of action of these commercially available molecules, these experiments indicate that such PTGS reporters can be exploited to conduct high-throughput screening in order to identify novel natural/synthetic compounds, microorganisms or extracts from micro- or macro-organisms that have the potential to promote disease resistance in cultivated plants by enhancing PTGS activity. Furthermore, such reporter system can also be used to elucidate the mode of action of compounds, microorganisms or extracts from micro- or macro-organisms with known antimicrobial activity in order to meet the requirement of the legislation for their commercialization.

SUMMARY

The subject-matter of the present invention is thus a method for screening natural or synthetic molecules, microorganisms or extracts from micro- or macro-organisms for their potential ability to inhibit pathogen entry, propagation or replication in plants through PTGS enhancement comprising the following steps:

(a) providing visual PTGS reporter plants transgenic for an inverted-repeat construct which triggers post-transcriptional gene silencing of an endogenous visual reporter gene driven by a tissue-specific promoter wherein said tissue is relevant for pathogen entry, propagation or replication, (b) applying said molecules or microorganisms or extracts on said plants, (c) visually observing plant changes translating an increase or decrease of said post-transcriptional gene silencing activity of said endogenous visual reporter gene.

Another subject-matter of the present invention is a method for characterizing the mode of action of natural or synthetic molecules, microorganisms or extracts from micro- or macro-organisms that are known to enhance plant disease resistance comprising the following steps:

(a) providing several types of visual PTGS reporter plants transgenic for an inverted-repeat construct which triggers post-transcriptional gene silencing of an endogenous visual reporter gene, each type driven by a different tissue-specific promoter wherein said tissue is relevant for pathogen entry, propagation or replication, (b) applying said molecules or microorganisms or extracts on said plants, (c) visually observing plant changes translating an increase or decrease of said post-transcriptional gene silencing activity of said endogenous visual reporter gene in one or several of said types of visual PTGS reporter plants.

Another subject-matter of the present invention is a transgenic plant comprising an inverted-repeat construct which triggers post-transcriptional gene silencing of an endogenous visual reporter gene driven by a tissue-specific promoter wherein said tissue is relevant for pathogen entry, propagation or replication.

Another subject-matter of the present invention is an isolated DNA with a hairpin structure comprising an inverted-repeat construct which triggers post-transcriptional gene silencing of an endogenous visual reporter gene under the control of a tissue-specific promoter.

Another subject-matter of the present invention is a vector comprising isolated DNA with a hairpin structure under the control of a promoter according to the invention.

Definitions

To "modulate" means to inhibit or to increase.

A "visual reporter gene" means a gene linked to a visual phenotype upon silencing of the said endogenous gene. Modulation of its expression is directly visualized by a phenotypic change that is detected with naked eyes.

A "tissue-specific promoter" means here a promoter that allows the expression of the inverted repeat exclusively in said tissue and with an activity that is strong enough to allow the visual detection of phenotypic changes upon silencing of an endogenous visual reporter gene.

A "tissue relevant for pathogen entry" means a tissue through which the pathogen enters in the host organism.

A "tissue relevant for pathogen propagation" means a tissue composing, or in the proximity of, the routes required for short or long distance pathogen colonization in plants.

An "extract" means the result of a chemical or physical process on a mixture or material, for example all or part of a macroorganism, preferably a plant, or a microorganism population, preferably an in vitro microorganism culture. The term "extract" comprises isolated natural molecules and compounds.

RNA silencing or interference (RNAi) is a valuable reverse genetics tool to study gene function in various organisms. The process of RNAi was initially described as a post-transcriptional gene silencing mechanism of gene regulation.

With the RNAi method, double-stranded RNA (dsRNA) can specifically lower the products—mRNA and/or protein—of a target gene when introduced into, or expressed from, an organism or cells derived from such organism. RNAi involves the processing of dsRNA precursors into short interfering RNA (siRNA) duplexes of approximately 21 to 24 nucleotides in length by Dicer enzymes, named DICER-like enzymes in plants. A selected strand, referred to as the guide strand, is incorporated into a RNA-induced silencing complex (RISC) containing an AGO protein, which is the catalytic component of RISC. The small RNA guide strand directs RISC onto sequence complementary mRNA targets to trigger their degradation and/or translational inhibition.

"Homology" is defined as the percentage of bases in the nucleotide sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

An "isolated" molecule is one that has been identified and separated and/or recovered from a component of its natural environment.

The terms "polypeptide", "peptide" or "protein" are used interchangeable throughout this specification.

To determine the percentage of homology between two amino acid sequences (e.g., one of the sequences encoded by a nucleic acid of the invention and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An "isolated" nucleic acid molecule is one molecule, which is substantially separated from other nucleic acid molecules, which are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism, from which the nucleic acid is derived.

Moreover, the term "polynucleotide" as used in accordance with the present invention encompasses variants of the aforementioned specific polynucleotides. Said variants may represent orthologs, paralogs or other homologs of the polynucleotide of the present invention. The polynucleotide variants, preferably, also comprise a nucleic acid sequence characterized in that the sequence can be derived by at least one nucleotide substitution, addition and/or deletion whereby the variant nucleic acid sequence shall still encode a polypeptide having a biological activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are, preferably, 0.1× SSC and 20° C. to 45° C., preferably between 30° C. and 45°

C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention.

A fragment as meant herein, preferably, comprises at least 20, at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences. Variant polynucleotides as referred to in accordance with the present invention may be obtained by various natural as well as artificial sources. For example, polynucleotides may be obtained by in vitro and in vivo mutagenesis approaches using the above mentioned specific polynucleotides as a basis. Moreover, polynucleotide being homologs or orthologs may be obtained from various species.

Binding as meant in this context refers to hybridization by Watson-Crick base pairing discussed elsewhere in the specification in detail. An oligonucleotide as used herein has a length of at most 100, at most 50, at most 40, at most 30 or at most 20 nucleotides in length which are complementary to the nucleic acid sequence of the polynucleotides of the present invention. The sequence of the oligonucleotide is, preferably, selected so that a perfect match by Watson-Crick base pairing will be obtained. The oligonucleotides of the present invention may be suitable as primers for PCR-based amplification techniques.

The term "dsRNA" refers to RNA having a duplex structure comprising two complementary and anti-parallel nucleic acid strands. Not all nucleotides of a dsRNA necessarily exhibit complete Watson-Crick base pairs; the two RNA strands may be substantially complementary. The RNA strands forming the dsRNA may have the same or a different number of nucleotides, with the maximum number of base pairs being the number of nucleotides in the shortest strand of the dsRNA. Preferably, the dsRNA is no more than 500, more preferably less than 400, and most preferably between 200 and 350, nucleotides in length. dsRNAs of this length are particularly efficient in inhibiting the expression of the target gene using inverted-repeat PTGS techniques. dsRNAs are subsequently processed by DCL enzymes into short interfering RNAs (siRNAs). RNAi is mediated by short interfering RNAs (siRNAs). The term "short interfering RNA" or "siRNA" refers to a nucleic acid molecule which is a double-stranded RNA agent that is complementary to i.e., able to base-pair with, a portion of a target RNA (generally mRNA), i.e. the polynucleotide of the present invention being RNA. siRNA molecules specifically guide RISC to silence the sequence complementary mRNA target.

By virtue of the specificity of the siRNA sequence and its homology to the RNA target, siRNA is able to cause cleavage and/or translational inhibition of the target RNA strand, thereby promoting its degradation and inhibiting mRNA translation. Preferably, the siRNA duplex which is sufficient to mediate RNAi comprises a duplex of nucleic acid sequence fragments of the coding region of the targeted candidate gene. Also preferably, a nucleic acid sequence encoding a siRNA or dsRNA (e.g. 250 bp) comprising a sequence sufficiently complementary to a target gene is operatively linked to an expression control sequence. Thus, the mediation of RNAi to inhibit expression of the target gene can be modulated by said expression control sequence.

The complementary regions of the siRNA or dsRNA allow sufficient hybridization of the siRNA or dsRNA to the target mRNA and thus mediate RNAi. The siRNA sequence needs to be of sufficient length to bring the siRNA and target RNA together through complementary base-pairing interactions. The siRNA used may be of varying lengths. The length of the siRNA is preferably greater than or equal to ten nucleotides and of sufficient length to stably interact with the target RNA; specifically 15-30 nucleotides; more specifically any integer between 15 and 30 nucleotides, most preferably 15, 16, 17, 18, 19, 20, 21, 22, 23, 24, 25, 26, 27, 28, 29, and 30. By "sufficient length" is meant an oligonucleotide of greater than or equal to 15 nucleotides that is of a length long enough to provide the intended function under the expected condition. By "stably interact" is meant interaction of the short interfering RNA with target nucleic acid (e.g., by forming hydrogen bonds with complementary nucleotides in the target under physiological conditions). Generally, such complementarity is 100% between the siRNA and the RNA target, but can be less if desired, preferably 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences.

Down-regulation as meant herein relates to a statistically significant reduction of the mRNA detectable in a cell, tissue or organism or even to a failure to produce mRNA in detectable amounts at all. This also includes the reduction of the stability of mRNA encoding all or a part of any sequence described herein. Moreover, down-regulation also encompasses an impaired, i.e. significantly reduced, production of protein from RNA sequences encoding all or a part of any sequence or even the absence of detectable protein production.

A "transgenic plant" is defined herein as a plant which is genetically modified in some way. The altered genetic material may encode a protein comprising a regulatory or control sequence or may be or include an antisense sequence or encode an antisense RNA or siRNA which inhibits the DNA or mRNA sequence or portion thereof responsible of the expression of the polypeptide of which a modification of the expression is foreseen.

A "transgene" or "transgenic sequence" is defined as a foreign gene or partial sequence which has been incorporated into a transgenic plant.

Transgenic plants made in accordance with the present invention may be prepared by DNA transformation using any method of plant transformation known in the art. Plant transformation methods include direct co-cultivation of plants, tissues or cells with *Agrobacterium tumefaciens* or direct infection; direct gene transfer into protoplasts or protoplast uptake; electroporation; particle bombardment; injection into meristematic tissues of seedlings and plants; injection into protoplasts of cultured cells and tissues. Generally a complete plant is obtained from the transformation process. Plants are regenerated from protoplasts, callus, tissue parts or explants, etc.

The term "microorganisms" comprises plant pathogen microorganisms and non-plant pathogen microorganisms.

The term "pathogen" means any disease producing agent, for example bacteria, fungi, oomycetes, viruses and compounds released or secreted from these pathogens or from parasites, for example effectors injected by insects or nematodes.

LEGENDS OF FIGURES

FIG. 1. $H_2O_2$ production upon bacteria perception is localized in tissues relevant for entry (hydathodes and stomata) and for bacterial propagation (vascular tissues).

$H_2O_2$ production as detected by DAB (diaminobenzedine) staining in WT plant after water (Mock) or *Pseudomonas fluorescens* infiltration at the level of stomata (A), hydathodes (B) and veins (C), respectively FIG. 2. PTGS-defective mutants exhibit a more pronounced entry and propagation of a virulent *Pseudomonas syringae* strain.

A. Wild type (WT) plants, hen1 and grp7-1 were sprayed with Pto-DC3000-GFP at $2 \cdot 10^7$ cfu/ml. GFP was monitored under UV light 2 day after inoculation.

B. Five-week-old plants of WT, rdr6-15 and dcl2dcl4 mutants were wound-inoculated with a toothpick in secondary veins (white circle) with Pto-DC3000-GFP at $5 \cdot 10^7$ cfu/ml. GFP is monitored under UV light at 5 day-post inoculation (dpi).

C. Five-week-old plants of WT, rdr6-1.5 and dcl2dcl4 mutants were wound-inoculated as in B. Pictures of bacterial disease symptoms were taken at 5 dpi.

FIG. 3. Phenotypes of some tissue/cell type-specific IR-PTGS sensors.

A. Schematic representation of the hairpin IR-SUL under the control of a tissue- or cell type-specific promoter B. Phenotypes of representative T1 transgenic plants expressing the hairpin IR-SUL (SUL-LUS) under the control of a cambium-specific promoter (WOX4-p), xylem-specific promoters (AAP6-p and IRX3-p), hydathode-specific promoter (miR164A-p) and guard cell-specific promoter (GC1-p).

FIG. 4. Formulated Fosetyl-Al and laminarine compounds enhance PTGS activity at within and around phloem companion cells.

A. Pictures of 5-week-old SUC-SUL plants treated for 4 days with formulated fosetyl-Aluminium referred to as Aliette B. Pictures of 5-week-old SUC-SUL plants treated for 4 days with formulated Laminarine.

C. Pictures of 5-week-old SUC-SUL plants treated for 4 days with formulated *Bacillus subtilis*.

FIG. 5. Molecular analysis on the SUC-SUL plants treated with salicylic acid.

A. Pictures of 5-week-old SUC-SUL plants treated either Mock (0.01% Silwet L-77 only) or 2 mM of SA (with 0.01% Silwet L-77) for 5 days.

B. RT-qPCR analysis depicting SUL and CIP4 transcript levels in SUC-SUL leaves treated with either Mock (0.01% Silwet L-77 only) or with 2 mM of SA (+0.01% Silwet L-77) for 3 days.

C. Western blot analyses showing SUL and CIP4 protein levels in SUC-SUL leaves treated with either Mock (0.01% Silwet L-77 only) or with 2 mM of SA (+0.01% Silwet L-77) for 3 days.

FIG. 6. Salicylic acid (SA) promotes PTGS activity within and around companion cells of the phloem but not in other tested tissue.

Picture of 5-week-old SUC-SUL, HYD-p::SUL-LUS, AAP6-p::SUL-LUS, IRX3-p::SUL-LUS or GC1-p::SUL-LUS plants treated either Mock (0.02% Silwet L-77 only) or 2 mM of SA (with 0.02% Silwet L-77) for 5 days.

DETAILED DESCRIPTION

The first subject-matter of the invention is a method for screening natural or synthetic molecules, microorganism and extracts from micro- or macro-organisms for their potential ability to inhibit pathogen entry, propagation or replication in plants through PTGS enhancement comprising the following steps:

(a) providing visual PTGS reporter plants transgenic for an inverted-repeat construct which triggers post-transcriptional gene silencing of an endogenous visual reporter gene driven by a tissue-specific promoter wherein said tissue is relevant for pathogen entry, propagation or replication, (b) applying said molecules or microorganisms or extracts on said plants, (c) visually observing plant changes translating an increase or decrease of said post-transcriptional gene silencing activity of said endogenous visual reporter gene.

Non-limitative examples of microorganisms (or their extracts) which can be screened for a modulation of RNA silencing activity using the method of the invention include:

Acetobacteraceae, Acidobacteriaceae, Actinospicaceae, Actinosynnemataceae, Addliaceae, Alcaligenaceae, Alicyclobacillaceae, Alteromonadaceae, Ardenscatenaceae, Aurantimonadaceae, Bacillaceae, Bacteriovoracaceae, Bartonellaceae, Bdellovibrionaceae, Beijerinckiaceae, Bradyrhizobiaceae, Brevibacteriaceae, Brucellaceae, Burkholderiaceae, Burkholderiales, Burkholderiales_incertae_sedis, Caldicoprobacteraceae, Caulobacteraceae, Cellulomonadaceae, Chitinophagaceae, Chloracidobacteria, Chloroflexaceae, Clostridiaceae, Comamonadaceae, Conexibacteraceae, Coxiellaceae, Cryomorphaceae, Cystobacteraceae, Cystobacterineae, Cytophagaceae, Deinococcaceae, Dermacoccaceae, Enterobacteriaceae, Enterococcaceae, Erythrobacteraceae, Eubacteriaceae, Exiguobacteraceae, Fimbriimonadaceae, Flavobacteriaceae, Frankiaceae, Gaiellaceae, Geobacteraceae, Geodermatophilaceae, Glycomycetaceae, Gracilibacteraceae, Haliangiaceae, Haloplasmataceae, Holophagaceae, Hyphomicrobiaceae, Hyphomonadaceae, Intrasporangiaceae, Kineosporiaceae, Koribacteraceae, Kouleothrixaceae, Lachnospiraceae, Leptospiraceae, Methylobacteriaceae, Methylo cystaceae, Methylophilaceae, Microbacteriaceae, Micrococcaceae, Micromonosporaceae, Mogibacteriaceae, Moraxellaceae, Mycobacteriaceae, Myxococcaceae, Nakamurellaceae, Nannocystaceae, Nitrosomonadaceae, Nitrospiraceae, Nocardiaceae, Nocardioidaceae, Oscillochloridaceae, Oxalobacteraceae, Oxalobacteraceae, Paenibacillaceae, Parachlamydiaceae, Patulibacteraceae, Pelobacteraceae, Peptostreptococcaceae, Phyllobacteriaceae, Piscirickettsiaceae, Planococcaceae, Polyangiaceae, Procabacteriaceae, Promicromonosporaceae, Propionibacteriaceae, Pseudomonadaceae, Pseudonocardiaceae, Rhizobiaceae, Rhodobacteraceae, Rhodobiaceae, Rhodocyclaceae, Rhodospirillaceae, Rickettsiaceae, Rikenellaceae, Roseiflexaceae, Saccharibacteria_genera_incertae_sedis, Sanguibacteraceae, Saprospiraceae, Sinobacteraceae, Solibacteraceae, Solirubrobacteraceae, Sphingobacteriaceae, Sphingomonadaceae, Spirochaetaceae, Sporichthyaceae, Sporolactobacillaceae, Staphylococcaceae, Streptomycetaceae, Streptosporangiaceae, Symbiobacteriaceae, Syntrophobacteraceae, Syntrophomonadaceae, Thermaceae, Thermoactinomycetaceae, Thermoanaerobacteraceae, Thermogemmatisporaceae, Thermomonosporaceae, Tissierellaceae, Turicibacteraceae, Veillonellaceae, Weeksellaceae, Williamsiaceae, Xanthobacteraceae, Xanthomonadaceae, Acaryochloridaceae, Alcaligenaceae, Alcanivoracaceae, Alteromonadaceae, Aquificaceae, Bacillaceae, Bacteroidaceae, Bradyrhizobiaceae, Burkholderiaceae, Campylobacteraceae, Carnobacteriaceae, Caulobacteraceae, Chlorobiaceae, Chloroflexaceae, Chromatiaceae, Chromatiales, Coeloplanidae, Co leofasciculaceae, Cyclobacteriaceae, Deferribacteraceae, Desulfobacteraceae, Desulfurellaceae, Ectothiorhodospiraceae, Erythrobacteraceae, Ferrimonadaceae, Flammeovirgaceae, Flavobacteriaceae, Aphanizomenonaceae, Aurantimonadaceae, Bacillaceae, Chitinophagaceae, Chromatiaceae, Comamonadaceae, Cyanothecaceae, Flaviobacteriaceae, Fusobacteriaceae, Halieaceae, Haloplasmataceae, Hyphomonadaceae, Intrasporangiaceae, Magnetococcaceae, Micrococcaceae, Nautiliaceae, Oceanospirillaceae, Phyllobacteriaceae, Piscirickettsiaceae, Pseudoalteromonadaceae, Pseudococcidae, Psychromonadaceae, Rhodobacteraceae, Sphingomonadaceae, Streptococcaceae, Synechococcaceae, Thermodesulfobacteriaceae, Thermotogaceae, Vibrionaceae, Flexibacteraceae, Haliangiaceae, Halobacteriaceae, Halomonadaceae, Helicobacteraceae, Hydrogenothe, maceae, Hyphomonadaceae, Idiomarinaceae, Intrasporangiaceae, Kordiimonadaceae, Lentisphaeraceae, Mariprofundaceae, Methanobacteriaceae, Methylococcaceae, Microbacteriaceae, Micromonosporaceae, Moraxellaceae, Myxococcaceae, Nautiliaceae, Nitrosopumilaceae, Nocardiaceae, Oceanospirillaceae, Paenibacillaceae, Parvularculaceae, Pelagibacteraceae, Pelobacteraceae, Peptococcaceae, Phyllobacteriaceae, Piscirickettsiaceae, Planctomycetaceae, Propionibacteriaceae, Pseudonocardiaceae, Rhizobiaceae, Rhodospirillaceae, Rhodothermaceae, Rivulariaceae, Saprospiraceae, Shewanellaceae, Sinorhizobium, Sphingomonadaceae, Spirochaetaceae, Synechococcaceae, Thermoanaerobacteraceae, Thermococcaceae, Thermotogaceae, Thermotogaceae, Verrucomicrobiae, Vibrionaceae, Xanthomonadaceae, Peridiniphycidae, Suessiaceae, Pyrocystaceae, Lophodiniaceae, Gloeodiniaceae, Tovelliaceae, Prorocentraceae, Gonyaulacaceae, Gymnodiniaceae, Hemidiniaceae, Symbiodiniaceae, Glenodiniopsidaceae, Blastodiniaceae, Goniodomataceae, Peridiniaceae, Ostreopsidaceae, Pyrophacaceae, Kareniaceae, Ceratiaceae, Ceratocoryaceae, Heterocapsaceae, Gonyaulax, Polykrikaceae, Oxytoxaceae, Ptychodiscaceae, Peridiniales, Gymnodiniales, Araphid-pennate, Bacillariophyta, Bangiaceae, Bathycoccaceae, Batrachospermales, Bo lidophyceae-and-relatives, Bonnemaisoniaceae, Braarudosphaeraceae, Callithamniaceae, Calyptrosphaeraceae, Ceramiaceae, Chaetopeltidales, Chaetophorales, Chlorarachnida, Chlorellales, Chlorodendrales, Chlorophyceae, Chlorophyta, Chrysochromulinaceae, Chrysoculteraceae, Chrysomerophyceae, Chrysophyceae-Synurophyceae, Cladophorales, Coccolithaceae, Coccolithales, Corallinales, Crustomastigaceae, Cryptomonadales, CW-Chlamydomonadales, Cyanidiales, Cyanophoraceae, Cyanoptycaceae, Dictyochales, Dictyochophyceae, Dinophyceae, Dolichomastigaceae, Do lichomastigales, Embryophyceae, Erythropeltidales, Euglenales, Euglenida, Eustigmatophyceae, Eutreptiales, Florenciellales, Florideophyceae, Gigartinales, Gonyaulacales, Mamiellaceae, Mamiellales, Mamiellophyceae, Marsupiomonadales, Mesostigmatophyceae, Microthamniales, Monomastigales, Nephroselmidaceae, Oedogoniales, Olisthodiscus, Oltmansiellopsidales, Pavlovaceae, Pedinellales, Pedinomonadales, Pedinophyceae, Pelagophyceae, Peridiniales, Phaeocystaceae, Phaeophyceae, Phaeothamniales, Pinguiochrysidaceae, Pleurochrysidaceae, Polar-centric-Mediophyceae, Porphyridiales, Prasinococcales, Prasiolales, Prorocentrales, Prymnesiaceae, Prymnesiophyceae, Pyramimonadales, Radial-centric-basal-Coscinodiscophyceae, Raphid-pennate, Raphidophyceae, Rhizochromulinales, Rhodellales, Rhodomelaceae, Rhodophyta, Rhodymeniales, Sphaeropleales, Spyridiaceae, Stylonemataceae, Suessiales, Synurales, Thoracosphaeraceae, Trebouxiophyceae, Trentepohliales, Ulotrichales, Ulvales-relatives, Vitrella, Watanabea-Clade, Wrangeliaceae, Xanthophyceae, Zygnemophyceae.

Non-limitative examples of macroorganism extracts which can be screened for a modulation of RNA silencing activity using the method of the invention are derived from algae, plants, insects or animals.

An additional step (d) allows the characterization of the effects of said molecules, microorganisms or extracts on PTGS enhancement and the quantification of the intensity by which they modulate RNA silencing in tissues that are relevant for pathogen entry, propagation or replication.

This additional step (d) is carried out by monitoring the levels of artificial siRNAs derived from said inverted-repeat and/or endogenous small RNAs and of artificial and/or endogenous small RNA targets.

For example, the levels of the 20-24 nt small RNA duplexes arising by the processing of the inverted repeat RNA RNase-III enzymes DICERs are monitored.

These level analyses will determine (i) at which steps of the RNA silencing pathway a given molecule, microorganism or extract is acting (small RNA biogenesis, accumulation and/or activity) (ii) the intensity by which a given molecule, microorganism or extract is modulating RNA silencing. Regarding the quantification of artificial or endogenous small RNA accumulation, Low Molecular Weight (LMW) Northern blot analyses or Real Time quantitative PCR (RT-qPCR) analyses can be used. Concerning the quantification of artificial or endogenous small RNA targets, High Molecular Weight (HMW) Northern analyses or RT-PCR analyses can be used.

Another subject-matter of the invention is a method for characterizing the mode of action of natural or synthetic molecules, microorganism and extracts from micro- or macro-organisms that are known to enhance plant disease resistance comprising the following steps:
(a) providing several types of visual PTGS reporter plants transgenic for an inverted-repeat construct which triggers post-transcriptional gene silencing of an endogenous visual reporter gene, each type driven by a different tissue-specific promoter wherein said tissue is relevant for pathogen entry, propagation or replication,
(b) applying said molecules, microorganisms or extracts on said plants, (c) visually observing plant changes translating an increase or decrease of said post-transcriptional gene silencing activity of said endogenous visual reporter gene in one or several of said types of visual PTGS reporter plants.

An additional step (d) allows the identification of molecules, microorganisms or extracts that have a tissue-specific effect or an effect on different tissues that are relevant for pathogen entry, propagation or replication.

This additional step (d) is carried out by comparing the visual effect between said types of visual PTGS reporter plants (i) wherein a tissue-specific effect means that said molecules, microorganisms or extracts are relevant for pathogens which entry, propagate or replicate only by said tissue or (ii) wherein an effect on different tissues means that said molecules, microorganisms or extracts are relevant for pathogens with different modes of entry, propagation or replication.

In one embodiment, post-transcriptional gene silencing is RNA silencing.

Said visual PTGS reporter plants are wild-type plants which have been transformed by a vector comprising an inverted-repeat construct. Said inverted-repeat construct, preferably a DNA sequence giving rise to a dsRNA polynucleotide with a hairpin structure, comprises an inverted-repeat of corresponding cDNA of said endogenous visual reporter gene or a fragment thereof. This inverted-repeat carries an intron sequence in the middle between the repeats to facilitate the folding of the dsRNA.

The inverted-repeat construct is under the control of a relevant tissue-specific promoter that is active enough to visualize phenotypic change due to the silencing of the endogenous visual reporter gene "Relevant" and "active enough" means that (i) the activity of the promoter has to be highly specific to the given tissue but also strong enough to produce small RNAs that trigger a visually detectable chlorosis within and around the given tissue; (ii) the promoter has to be as less as possible responsive to hormone or pathogen elicitors.

The inverted-repeat construct triggers post-transcriptional gene silencing of an endogenous visual reporter gene.

Preferably, the inverted-repeat construct comprises a sense and an antisense sequences, possibly separated by an intron or a fragment of an intron.

Most preferably, the inverted-repeat construct comprises the sense and antisense sequences of the SUL gene.

The sense sequence has a high degree of homology with the cDNA of the endogenous visual reporter gene, preferably more than 90%, more preferably more than 95%, the most preferably more than 99% of homology.

Preferably, the sense sequence is the cDNA of the endogenous visual reporter gene or a fragment thereof.

Said tissue-specific promoter is preferably selected in the group consisting of AAP6-p, IRX3-p, GC1-p, HYD-p, MYB60-p, CAB3-p, MYC1-p, WOX4-p and AHA3-p.

The inverted-repeat RNA polynucleotide is processed in said transgenic plants into siRNA duplexes.

These artificial siRNAs modulate the expression of said wild-type endogenous visual reporter gene expressed by said plants.

If PTGS is enhanced, post-transcriptional gene silencing of said endogenous visual reporter gene is increased and the expression of said endogenous visual reporter gene is thus decreased.

If PTGS is decreased, post-transcriptional gene silencing of said endogenous visual reporter gene is decreased and the expression of said endogenous visual reporter gene is thus increased.

For example with an endogenous visual reporter gene involved in chlorophyll biosynthesis in leaves:
   if PTGS is enhanced, the expression of said endogenous visual reporter gene is decreased and an enhanced visual chlorotic phenotype appears wherein and/or nearby tissues/cell types where the inverted-repeat is expressed i.e. in the target tissue of said tissue-specific promoter,
   if PTGS is decreased, the expression of said endogenous visual reporter gene is increased and a weaker chlorotic phenotype is observed wherein and/or nearby tissues/cell types where the inverted-repeat is expressed i.e. in the target tissue of said tissue-specific promoter.

For example with an endogenous visual reporter gene involved in chlorophyll biosynthesis in leaves and a promoter specific of hydathode tissues:
   if PTGS is enhanced, the expression of said endogenous visual reporter gene is decreased and an enhanced chlorotic phenotype appears at the level of and/or nearby hydathodes,
   if PTGS is decreased, the expression of said endogenous visual reporter gene is increased and a weaker chlorotic phenotype is observed at the level of and/or nearby hydathodes.

In step (b), said molecule, microorganism or extract can be applied either at seedling stage or at later developmental stages such as at rosette stage. This molecule, microorganism or extract is applied either in liquid medium in (micro) well-plates, by infiltration using a needle-less syringe or vacuum, or by spray using a concentration of surfactant that is known from people skilled in the art.

Visual observation of step (c) can be made several days, preferably 4 to 5 days, after step (b) The term "silencing" means down-regulating or antagonizing, at least partly, a targeted gene transcript.

In one embodiment, said silencing of the method according to the invention is temporary.

"Temporary" means reversible in several weeks, preferably several days.

Another subject-matter of the present invention is a transgenic plant comprising an inverted-repeat construct which triggers post-transcriptional gene silencing of an endogenous visual reporter gene driven by a tissue-specific promoter wherein said tissue is relevant for pathogen entry, propagation or replication and active enough in the dedicated tissues or cell types targeted Preferably, said tissue relevant for pathogen entry, propagation or replication is relevant for pathogen entry and/or short distance propagation and/or long distance propagation and/or replication.

Preferably, said tissue relevant for pathogen entry is selected in the group consisting of hydathodes, guard cells, the base of trichomes and epidermal cells.

Preferably, said tissue relevant for short or long distance propagation of pathogens in the vasculature is selected in the group consisting of cambium cells, xylem parenchyma cells or phloem companion cells.

Preferably, said tissue relevant for pathogen replication is selected in the group consisting of mesophyll cells.

Preferably, said endogenous visual reporter gene is involved in pigment biosynthesis, preferably in chlorophyll biosynthesis, preferably in aerial part of said plants.

More preferably, said endogenous visual reporter gene is the Chlorina42 (CH42) gene, known also as the SULPHUR (SUL) gene. Its cDNA is SEQ ID NO:1.

Preferably, said plants are selected in the group consisting of model plants, preferably *Arabidopsis thaliana* or agronomical plants, preferably cereals.

Preferably, said pathogen is selected in the group consisting of bacteria, fungi, oomycetes and viruses.

Preferably, said inverted-repeat construct is SEQ ID NO:2.

In one embodiment, said tissue-specific promoter is selected in the group consisting of AAP6 promoter of SEQ ID NO:4, IRX3 promoter of SEQ ID NO:5, GC1 promoter of SEQ ID NO:6, HYD promoter of SEQ ID NO:7, AHA3 promoter of SEQ ID NO: 8, MYC1 promoter of SEQ ID NO: 9, MYB60-derived promoter of SEQ ID NO: 10, CAB3 promoter of SEQ ID NO: 11, WOX4 promoter of SEQ ID NO: 12, BDG promoter of SEQ ID NO:37.

Another subject-matter of the present invention is an isolated dsRNA with a hairpin structure comprising an inverted-repeat construct which triggers post-transcriptional gene silencing of an endogenous visual reporter gene under the control of a tissue-specific promoter.

Another subject-matter of the present invention is an isolated dsRNA with a hairpin structure comprising SEQ ID NO:2 under the control of a tissue-specific promoter.

Another subject-matter of the present invention is an isolated dsRNA with a hairpin structure of SEQ ID NO:3.

Another subject-matter of the present invention is a vector comprising an isolated dsRNA with a hairpin structure comprising SEQ ID NO:2 under the control of a tissue-specific promoter or an isolated dsRNA with a hairpin structure of SEQ ID NO:3.

Examples

Material and Methods
DNA Constructs

To generate the plasmids expressing a hairpin of the SUL gene (AT4G18480) under the control of a tissue-specific promoter, a MultiSite Gateway® (Invitrogen) strategy was used. The tissue-specific promoters (AAP6-p, IRX3-p, GC1-p, HYD-p, WOX4-p, CAB3-p, MYC1-p, MYB60-p, BDG-p and AHA3-p) were amplified by 2 steps-PCR with specific primers (see Table n° 1) using genomic DNA isolated from *Arabidopsis thaliana* leaves. The resulting PCR were introduced into the pDON vector pDON221_P1P5r (Invitrogen) using the BP clonase enzyme mix (Invitrogen).

To generate the plasmid encoding for the SUL hairpin (pDON221_SUL-LUS), PCR product of 200 nt containing NcoI site was generated with specific primers (see Table n° 1) using pK7WG2D as a template. The resulting PCR product was introduced into the pDON221_P5P2 (Invitrogen) to give pDON221_P5P2_NcoI. The SUL hairpin fragment was purified from the NcoI-digested plasmid atSUC2-SUL-LUS (Himber et al., 2003). The resulting fragment was inserted as a NcoI restriction fragment into pDON221_P5P2_NcoI. Each plasmid containing a tissue-specific promoter is recombined in presence of pDON221_SUL-LUS and the pDEST plasmid pB7WG (Karimi et al., 2002) using the LR clonase plus enzyme mix (Invitrogen) to give the following plasmids: AAP6-p::SUL-LUS, IRX3-p::SUL-LUS, HYD-p::SUL-LUS, GC1-p::SUL-LUS, WOX4-p::SUL-LUS, CAB3-p::SUL-LUS, MYC1-p::SUL-LUS, MYB60-p::SUL-LUS and AHA3-p::SUL-LUS.

Transgenic Plants

*Arabidopsis thaliana* grp7-1, rdr6, dcl2dcl4 and hen1-1 were described previously (Zu et al., 2007; Xie et al., 2005; Chen et al., 2002)

Transformation of the AAP6-p::SUL-LUS, IRX3-p::SUL-LUS, HYD-p::SUL-LUS, GC1-p::SUL-LUS, WOX4-p::SUL-LUS, MYC1-p::SUL-LUS, MYB60-p::SUL-LUS, BDG-p::SUL-LUS and AHA3-p::SUL-LUS constructs in Col-0 with *Agrobacterium* strain GV3101 was performed as described previously (Bechtold et al., 1993). Selection was on medium containing 10 mg/l DL-Phosphinothricin (Sigma aldrich). Pictures of 4-weeks old T1 transgenic plants were taken.

Bacterial Infection

*Pseudomonas syringae* pv. tomato DC3000 (Pto DC3000) carrying a GFP-encoding plasmid (Badel et al., 2002) was grown at 28° C. in NYGB medium (5 g $L^{-1}$ bactopeptone, 3 g $L^{-1}$ yeast extract, 20 ml $L^{-1}$ glycerol) containing rifampicin (25 mg $mL^{-1}$) for selection.

Bacteria infections were performed by spray inoculation or by wound inoculation in secondary veins. For the spray assay, the bacteria Pto DC3000-GFP was used at $2·10^7$ cfu/ml supplemented with 0.005% of Silwet L-77 (Lehle Seeds). For wound inoculation, Pto DC3000-GFP was used at $5·10^7$ cfu/ml and inoculated in secondary veins using a toothpick. The plants were covered with a lid during all the time of the experiment. GFP is monitored under UV light at 2 days (FIG. 1A) or 5 days (FIG. 1B) post inoculation (dpi).

*Pseudomonas fluorescens* was inoculated by infiltration at $1·10^8$ cfu/ml into the leaves. Forty-eight hours later, the infiltrated leaves were collected and chlorophyll was cleared by using lactophenol (lactic acid:glycerol:water:phenol; 1:1:1:1). Leaves were then incubated with 3,3'-Diaminobenzidine (1 mg·$ml^{-1}$; pH 3.5) for 3 hours to stain hydrogen peroxide ($H_2O_2$) molecules.

TABLE NO 1

| Name of the plasmid | Name of oligos | Sequence of the oligos | SEQ ID NO: |
|---|---|---|---|
| pDON_P1P5r_pAAP6 | pDON_P1_pAAP6_F | AAAAAGCAGGCT gctgatgctgttattaatagt | 13 |
|  | pDON_P5r_pAAP6_R | TATACAAAGTTG ctatcgattgtattgagctta | 14 |
| pDON_P1P5r_pHYD | pDON_P1_pHYD_F | AAAAAGCAGGCT aagttaggacaacacgcaaa | 15 |
|  | pDON_P5r_pHYD_R | TATACAAAGTTG tggagattctcacccgcat | 16 |
| pDON_P1P5r_pIRX3 | pDON_P1_pIRX3_F | AAAAAGCAGGCT cagaattcaagtagctgccca | 17 |
|  | pDON_P5r_pIRX3_R | TATACAAAGTTG agggacggccggagatta | 18 |

TABLE NO 1-continued

Oligonucleotides used for clonings.

| Name of the plasmid | Name of oligos | Sequence of the oligos | SEQ ID NO: |
|---|---|---|---|
| pDON_P1P5r_pGC1 | pDON_P1_pGC1_F | AAAAAGCAGGCT tttggaacactctaccaacg | 19 |
|  | pDON_P5r_pGC1_R | TATACAAAGTTG atacttgagtagtgatatgaa | 20 |
| pDON_P1P5r_pWOX4 | pDON_P1_WOX4_F | AAAAAGCAGGCT ggcaagtgtagtggaggagg | 21 |
|  | pDON_P5r_WOX4_R | TATACAAAGTTG tgctatatgttaaaactagcaaatgc | 22 |
| pDON_P1P5r_pAHA3 | pDON_P1_pAHA3_F | AAAAAGCAGGCT aataactacgtatatgctgggaag | 23 |
|  | pDON_P5r_pAHA3_R | TATACAAAGTTG gtggactacgttaggctatttg | 24 |
| pDON221_P5P2_NcoI | pDON_P5_Kan_NcoI_F | ATACAAAGTTG aggatgatctggacgaagag | 25 |
|  | pDON_P2_Kan_NcoI_R | AGAAAGCTGGGT tgtcctgatagcggtccgc | 26 |
|  | adap_attB2 | GGGGACCACTTTGTACAAGAAAGCTGGGT | 27 |
|  | adap_attB5 | GGGGACAACTTTGTATACAAAGTTG | 28 |
|  | adap_attB1 | GGGGACAAGTTTGTACAAAAAAGCAGGCT | 29 |
|  | adap_attB5r | GGGGACAACTTTTGTATACAAAGTTG | 30 |
| pDON_P1P5r_pMYC1 | pDON_P1_pMYC1_F | AAAAAGCAGGCT gaggttcaaatcaatatgaaatcc | 31 |
|  | pDON_P5r_pMYC1_R | TATACAAAGTTG aggagacaaccaaaaggcaaaat | 32 |
| pDON_P1P5r_pMYB60 | pDON_P1_pMYB60_F | AAAAAGCAGGCT cgtgtggagatcaacatatcttc | 33 |
|  | pDON_P5r_pMYB60_R | TATACAAAGTTG catctctctctctcttcctc | 34 |
| pDON_P1P5r_pCAB3 | pDON_P1_pCAB3_F | AAAAAGCAGGCT aaatcaagagaaatgtgattctcg | 35 |
|  | pDON_P5r_pCAB3_R | TATACAAAGTTG gattgaaaatggttaggtagggtt | 36 |
| pDON_P1_pBDG | pDON_P1_pBDG_F | AAAAAGCAGGCTgatgccacgcacacgtcc | 38 |
|  | pDON_P5r_pBDG_R | TATACAAAGTTGgctgtggagatgagtcagt | 39 |

EXAMPLES

Example 1: PTGS Restricts Pathogen Entry and Propagation

Hydathodes and stomata are two major entry sites for endophytic colonization of foliar pathogens. Stomata are small pores located on the leaf surface that are surrounded by pairs of specialized parenchyma cells termed guard cells that regulate the aperture and closure of stomata to facilitate exchange of gases with the environment. Hydathodes are stomata-like structures located at the margin or tips of plant leaves. They are supposedly permanently open water pores that are closely associated with the ends of the leaf vascular system. Importantly, plants have evolved sophisticated active defense mechanisms to prevent pathogen entry at the level of hydathodes and stomata, and pathogen propagation in the vasculature. For instance, the recognition of the non-pathogenic bacteria *Pseudomonas fluorescens* leads to a strong production of hydroxide peroxide ($H_2O_2$) molecules at the level of hydathodes, guard cells and within and around the vasculature likely to limit the entry and propagation of bacterial pathogens and perhaps other type of pathogens (FIGS. 1A, B and C). However, the role of PTGS in orchestrating such defense responses remains elusive. To determine the physiological relevance of PTGS in restricting pathogen entry, the inventors have first analyzed the ability of the model pathogenic bacterium *Pseudomonas syringae* pv. tomato strain DC3000 (Pto DC3000) to enter through hydathodes and stomata from *Arabidopsis* WT and PTGS-defective mutant leaves. For this purpose, they have spray inoculated 5-week-old leaves from *Arabidopsis* WT, hen1-1 and grp7-1 mutants—both hen1-1 and grp7-1 mutant are impaired in RNA silencing—with a virulent Pto DC3000 strain expressing the Green Fluorescence Reporter (GFP) protein and have further monitored the GFP signal during the course of the infection under UV light. Interestingly, results from these analyses revealed a pronounced GFP signal in hydathodes of hen1-1-infected mutant leaves as early as 2 day-post inoculation (dpi) that was absent from hydathodes of WT-infected leaves (FIG. 2A). Enhanced GFP signal was also obtained within and around stomata from grp7-1-infected leaves as compared to WT-infected leaves at 2 dpi (FIG. 2A). Overall, these results indicate that PTGS plays a major role in restricting the entry of Pto DC3000 at both the level of hydathodes and stomata. These results also suggest that PTGS is likely active in these tissues/cell types as previously reported in guard cells (Yang et al., 2008).

Once inside the intercellular space of plant leaves, foliar biotrophic pathogens use different strategies to colonize distal plant tissues. For example, RNA viruses use alive phloem tissues as a major route to propagate in systemic tissues and this viral spreading is restricted by PTGS. As an example, Arabidopsis mutants that are defective in the two major antiviral Dicer-like 2 (DCL2) and DCL4 exhibit long distance propagation of several RNA viruses (Deleris et al., 2006; Diaz-Pendon et al., 2007; Qu et al., 2008). By contrast, fungal, oomycete and bacterial pathogens can spread in distal plant tissues through xylem vessels, which are dead cells that transport nutrients and water from the root to the aerial part of the plant. However, it is not known whether PTGS plays any role in restricting the propagation of such non-viral pathogens within and around xylem vessels. To test this idea, the inventors have wound-inoculated leaf secondary veins from WT and the PTGS-defective mutants dcl2/dcl4 and rdr6-15 with the virulent Pto DC3000-GFP strain, which propagates exclusively through Arabidopsis xylem vessels (Yu et al., 2013), and have further monitored GFP signal along the leaf vascular tissues of these different genotypes. Results from these analyses revealed a significant increase in bacterial spreading in both dcl2/dcl4 and rdr6-15-infected mutant leaves as compared to WT-infected leaves (FIG. 2B), which was associated with enhanced disease symptoms in tissues that surround the leaf vasculature of these PTGS-defective mutants (FIG. 2C). These results indicate that PTGS plays also a critical role in restricting Pto DC3000 propagation within and around leaf vasculature. Furthermore, they suggest that PTGS might be active in tissues/cell types that surround xylem vessels such as xylem parenchyma cells, cambial cells and phloem tissues, which is consistent with previous reports showing that IR-PTGS is effective in phloem companion cells (Smith et al., 2010; Dunoyer et al., 2005; de Felippes et al., 2011).

Example 2: Silencing of the SUL Endogene is Effective in Tissues/Cell Types that are Relevant for Pathogen Entry and Propagation Providing that a Promoter that is Specific and Active Enough is Used to Drive the Expression of the Inverted Repeat The results obtained in Example 1 prompted the inventors to generate PTGS sensors in tissue/cell types that are physiologically relevant for pathogen entry and/or propagation. Additionally, they decided to generate PTGS sensors in cell types that are relevant for pathogen replication i.e mesophyll cells and for the entry of the majority of fungal or oomycete pathogens i.e epidermal cells. Given that plants produce a variety of small RNA-dependent PTGS pathways that involve common or specific plant silencing factors, they decided to generate biosensors from a well-characterized PTGS pathway that is functionally relevant for biotic stress responses: the inverted repeat PTGS (IR-PTGS) pathway. These PTGS sensors were all designed to silence the SUL (At4g18480) endogene in hydathodes, guard cells, xylem parenchyma cells, vascular meristematic cells (cambial cells), phloem companion cells, cells surrounding the base of trichomes or mesophyll cells. All these tissue- or cell type-specific PTGS sensors were produced in the reference Arabidopsis accession Columbia (Col-0).

To generate IR-PTGS sensors, the inventors have first generated constructs containing an hairpin that carries sequence homology with the SUL endogene under the control of the tissue- or cell type-specific xylem promoter, guard cell promoter, hydathode promoter, cambium promoter, mesophyll promoter and base of trichome promoter. Among the Arabidopsis encoding genes, the inventors selected tissue-specific promoters that fulfil several criteria: (i) the activity of the promoter has to be highly specific to the given tissue but also strong enough to produce small RNAs that trigger a visually detectable chlorosis in the given tissue; (ii) the promoter has to be as less as possible responsive to hormone or pathogen elicitors. After extensive bibliographic research and analyses of mRNA-seq datasets, the inventors selected the following promoters: AAP6 promoter: active in xylem parenchyma cells and in meristematic vascular cells (Okumoto et al., 2002), IRX3 promoter: active in xylem parenchyma cells (Gardiner et al., 2003), GO and MYB60 promoters: active in guard cells (Yang et al., 2008), AtmiR164A truncated promoter: active in hydathodes (Nikovics et al., 2006), WOX4 promoter: active in meristematic vascular cells (Hirakawa et al., 2010), MYC1 promoter: active at the base of trichome (Zhao et al., 2012), AHA3 promoter: active in phloem companion cells (DeWitt et al., 1991), BDG promoter: active in epidermal cells (Kurdyukov et al., 2006) or CAB3 promoter: active in mesophyll cells (Susek et al., 1993). It is noteworthy that the SUL hairpin has been previously described and triggers IR-PTGS through well-characterized Arabidopsis silencing factors such as DCL4 and AGO1 (Dunoyer et al., 2005; Brodersen et al., 2008). All these constructs were further cloned into the binary vector pB7WG and transformed in the Arabidopsis Col-0 accession. Examples of the phenotypes obtained from the WOX4-p:IR-SUL, the AAP6-p:IR-SUL, the IRX3-p:IR-SUL and the GC1-p:IR-SUL and the miR164A-p:IR-SUL primary transformants are depicted in FIG. 3B. Interestingly, all these Arabidopsis reference lines, except WOX4-p:IR-SUL, display a chlorotic phenotype in the tissues and cell types of interest (FIG. 3B), as well as in cells that surround the siRNA production site (data not shown), which is consistent with previous reports showing non-cell autonomous effects triggered by artificial siRNAs directed against the SUL gene (Dunoyer et al., 2005; de Felippes et al., 2011). Overall, these results indicate that IR-PTGS is effective in hydathodes, xylem tissues and guard cells. The authors were not able to detect visually a chlorotic phenotype in homozygous WOX4-p:IR-SUL transgenic plants (FIG. 3B). Several reasons can account for the absence of chlorosis: (i) the WOX4 promoter activity is not strong enough to produce the minimal amount of small RNA required to trigger IR-PTGS mediated chlorosis or (ii) IR-PTGS is not effective in the vascular cambium. For this reason, the authors selected other promoters such as the AAP6 promoter that is significantly expressed in both cambial cells and xylem parenchyma cells. These biosensors are thus valuable resources to monitor IR-PTGS activity in tissues and/or cell types that are relevant for pathogen entry, propagation or replication.

Example 3: Proof-of-Concept Experiment: Formulated and Active Compounds that are Known to Promote Disease Resistance in Agriculturally Important Crops can Elevate PTGS Activity on a Specific Arabidopsis Silencing Reporter To determine whether the above Arabidopsis PTGS sensors represent promising biosensors to identify solutions to enhance disease resistance, the inventors have tested whether formulated or active compounds, which are known to induce plant disease resistance in cultivated plants, can also enhance PTGS activity on the above silencing reporter systems. For this purpose, they have sprayed a previously characterized phloem-specific IR-PTGS sensor (Dunoyer et al., 2005) with either (1) Salicylic acid (SA), a well-characterized phytohormone that plays a critical role in resistance against biotrophic pathogens, (2) 2,6-dichloroisonicotonic acid and benzo-(1,2,3)-thiadiazole-7-carbothioic acid S-methyl ester (BTH), a functional analog of SA that is regularly used by farmers to enhance disease resistance in crops, (3) Aliette, formulated fosetyl-Aluminium that can stimulate plant antimicrobial defense in cultivated plants but also protect them from fungal and oomycete infections through a potent and systemic fungicide activity, (4) Serenade, which is composed of formulated *Bacillus subtilis* (5) formulated Laminarine, a beta 1-3 glucan that mimics fungal cell wall and therefore promote natural antifungal defense responses in some cultivated plants; and have further monitored the effects of such treatments on the vein-centered chlorotic phenotype of this IR-PTGS reporter system. Interestingly, with the exception of Serenade (FIG. 4), all the above treatments led to a significant enhanced chlorotic phenotypes indicating stronger IR-PTGS activity in these challenged plants (FIGS. 4, 5 and 6). It is noteworthy that Aliette was the most potent inducer of IR-PTGS as revealed by a very strong and spreading chlorotic phenotype throughout the IR-PTGS sensor leaves, even at low concentrations, while the formulated Laminarine compound gave a mild but yet detectable enhanced chlorotic phenotype (FIG. 4 and data not shown). Further molecular analyses conducted in the SA-treated leaf samples revealed a significant decrease in SUL protein levels with a mild reduction in SUL transcript accumulation (FIG. 5), supporting a role for SA in promoting IR-PTGS activity particularly by inhibiting protein production. Moreover, no significant effect on the accumulation of artificial siRNAs was observed upon SA treatment at the concentration used (data not shown). It is noteworthy that the presented molecular analyses allow us (i) to detect at which steps of the PTGS a given molecule is acting (small RNA biogenesis and/or RISC activity) (ii) to quantify the strength by which the candidate molecules is modulating RNA silencing in a given tissue that is relevant for disease management. We thus conclude that these reporters can be used not only to easily and rapidly identify compounds that modulate RNA silencing—through a modulation of the chlorotic phenotype—but also to quantify their effects on RNA silencing activity and likewise on plant immunity (compounds that will have the potential to significantly enhance plant immune responses will likely be the ones that trigger a strong chlorotic phenotype and a strong decreased accumulation in the SUL and endogenous small RNA target levels).

To test whether the increase level of PTGS detected in SA-treated phloem-specific IR-PTGS sensor is detectable to other tissues, the inventors have sprayed different tissue-specific biosensors with the same concentration of SA. The biosensors specific to hydathodes, xylem parenchyma cells, guard cells and companion cells of phloem were sprayed with SA and the level of chlorosis was assessed 5 day later (FIG. 6). Interestingly, the above treatment led to a significant enhanced chlorotic phenotype only on the phloem-specific reporter but not in other silencing reporter tested (FIG. 6) suggesting that SA treatment induces PTGS activity specifically into phloem tissue. Therefore, all the leaf tissues do not respond similarly to a given molecule indicating that a molecule can induce PTGS in a tissue-specific manner. These observations therefore highlight the importance of using different tissue-specific biosensors to screen natural or synthetic compounds, microorganisms, macro- or microorganism extracts that can have a PTGS inducer activity specifically in a given tissue that is relevant to manage a specific disease. On the contrary, we are anticipating that the whole series of reporters will be also exploited to identify molecules, microorganisms or extracts that can induce PTGS/immune responses in all the above tissues. Such compounds, microorganisms or extracts will have the potential to confer broad-spectrum disease resistance and to restrict growth of pathogens with different modes of entry, propagation and replication. They will thus be the most relevant to increase disease resistance against a wide range of pathogens with different lifestyles.

Overall, these results provide 'proof-of-concept' data for the use of the above tissue/cell type specific IR-PTGS sensors to determine the mode of action of natural or synthetic compounds that are known to promote disease resistance in cultivated plants. Furthermore, given that (i) the tissue/cell type specific chlorotic phenotypes are detectable at seedlings stage (data not shown) (ii) the gain of PTGS activity is easily scorable in response to active or formulated compounds within few days post-treatment (FIGS. 4, 5 and 6), the above IR-PTGS sensors are thus well-suited for high-throughput screening of natural or synthetic compounds that can promote disease resistance in cultivated plants by enhancing PTGS activity.

Bechtold, N., Ellis, J. and Pelletier, G. (1993) In planta *Agrobacterium* mediated gene transfer by infiltration of adult *Arabidopsis thaliana* plants. C. R. Acad. Sci. Paris, Life Sciences, 316, 1194-1199.

Bologna N G, Voinnet O. (2014) The diversity, biogenesis, and activities of endogenous silencing small RNAs in *Arabidopsis*. Annu Rev Plant Biol. 65:473-503.

Boller T, Felix G. (2009) A renaissance of elicitors: perception of microbe-associated molecular patterns and danger signals by pattern-recognition receptors. Annu Rev Plant Biol.; 60:379-406

Brodersen P, Sakvarelidze-Achard L, Bruun-Rasmussen M, Dunoyer P, Yamamoto Y Y, Sieburth L, Voinnet O. (2008) Widespread translational inhibition by plant miRNAs and siRNAs. Science. 30; 320(5880):1185-90.

Chen X, Liu J, Cheng Y, Jia D (2002) HENT functions pleiotropically in *Arabidopsis* development and acts in C function in the flower. Development 129 (5): 1085-94.

Dalmay T, Hamilton A, Rudd S, Angell S, Baulcombe D C. (2000) An RNA-dependent RNA polymerase gene in *Arabidopsis* is required for posttranscriptional gene silencing mediated by a transgene but not by a virus. Cell. 26; 101(5):543-53.

Deleris A, Gallego-Bartolome J, Bao J, Kasschau K D, Carrington J C, Voinnet O. (2006). Hierarchical action and inhibition of plant Dicer-like proteins in antiviral defense. Science. 313(5783):68-71.

de Felippes F F, Ott F, Weigel D. (2011) Comparative analysis of non-autonomous effects of tasiRNAs and miRNAs in *Arabidopsis thaliana*. Nucleic Acids Res. 39(7):2880-9.

Diaz-Pendon J A, Li F, Li W X, Ding S W. (2007) Suppression of antiviral silencing by cucumber mosaic virus 2b protein in *Arabidopsis* is associated with drastically reduced accumulation of three classes of viral small interfering RNAs. Plant Cell. 19(6):2053-63.

DeWitt, N D, Harper, J F, Sussman, M. R. (1991) Evidence for a plasma membrane proton pump in phloem cells of higher plants. Plant J. 1:121-128.

Dou D, Zhou J M. (2012) Phytopathogen effectors subverting host immunity: different foes, similar battleground. Cell Host Microbe. 18; 12(4):484-95.

Dunoyer P, Himber C, Voinnet O. (2005) DICER-LIKE 4 is required for RNA interference and produces the 21-nucleotide small interfering RNA component of the plant cell-to-cell silencing signal. Nat Genet. 37(12): 1356-60.

Ellendorff U, Fradin E F, de Jonge R, Thomma B P. (2009) RNA silencing is required for *Arabidopsis* defence against Verticillium wilt disease. J Exp Bot. 60(2):591-602.

Fahlgren N, Howell M D, Kasschau K D, Chapman E J, Sullivan C M, Cumbie J S, Givan S A, Law T F, Grant S R, Dangl J L, Carrington J C. (2007) High-throughput sequencing of *Arabidopsis* microRNAs: evidence for frequent birth and death of MIRNA genes. PLoS One. 14; 2(2)

Frerigmann H, Böttcher C, Baatout D, Gigolashvili T. (2012) Glucosinolates are produced in trichomes of *Arabidopsis thaliana*. Front Plant Sci. 30; 3:242.

Fu Z Q, Guo M, Jeong B R, Tian F, Elthon T E, Cerny R L, Staiger D, Alfano J R (2007) A type III effector ADP-ribosylates RNA-binding proteins and quells plant immunity. Nature. 2007 May 17; 447(7142):284-8.

Gardiner J C, Taylor N G, Turner S R. (2003). Control of cellulose synthase complex localization in developing xylem. Plant Cell. 15(8):1740-8.

Hamilton A J, Baulcombe D C. (1999) A species of small antisense RNA in posttranscriptional gene silencing in plants. Science. 29; 286(5441):950-2.

Hirakawa Y, Kondo Y, Fukuda H. (2010) TDIF peptide signaling regulates vascular stem cell proliferation via the WOX4 homeobox gene in *Arabidopsis*. Plant Cell. 22(8): 2618-29.

Horbach R, Navarro-Quesada A R, Knogge W, Deising H B. (2011) When and how to kill a plant cell: infection strategies of plant pathogenic fungi. J Plant Physiol. 1; 168(1):51-62

Hugouvieux V, Barber C E, Daniels M J. (1998) Entry of *Xanthomonas campestris* pv. *campestris* into hydathodes of *Arabidopsis thaliana* leaves: a system for studying early infection events in bacterial pathogenesis. Mol Plant Microbe Interact. 1998 11(6):537-43.

Jakoby M J, Falkenhan D, Mader M T, Brininstool G, Wischnitzki E, Platz N, Hudson A, Hülskamp M, Larkin J, Schnittger A. (2008) Transcriptional profiling of mature *Arabidopsis* trichomes reveals that NOECK encodes the MIXTA-like transcriptional regulator MYB106. Plant Physiol. 2008 148(3):1583-602.

Ji L, Chen X. (2012) Regulation of small RNA stability: methylation and beyond. Cell Res. 22(4):624-36.

Jones J D, Dangl J L. (2006) The plant immune system. Nature. 16; 444(7117):323-9

Karimi M, Inzé D, Depicker A. (2002) GATEWAY vectors for *Agrobacterium*-mediated plant transformation. Trends Plant Sci. 7 (5): 193-5.

Li J, Yang Z, Yu B, Liu J, Chen X (2005) Methylation protects miRNAs and siRNAs from a 3'-end uridylation activity in *Arabidopsis*. Curr Biol. 23; 15(16):1501-7.

Li Y, Zhang Q, Zhang J, Wu L, Qi Y, Zhou J M. (2010) Identification of microRNAs involved in pathogen-associated molecular pattern-triggered plant innate immunity. Plant Physiol. 152(4):2222-31.

Melotto M, Underwood W, Koczan J, Nomura K, He S Y. (2006) Plant stomata function in innate immunity against bacterial invasion. Cell. 8; 126(5):969-80.

Mendgen K, Hahn M. (2002) Plant infection and the establishment of fungal biotrophy. Trends Plant Sci. 2002 7(8):352-6.

Mourrain P, Béclin C, Elmayan T, Feuerbach F, Godon C, Morel J B, Jouette D, Lacombe A M, Nikic S, Picault N, Rémoué K, Sanial M, Vo T A, Vaucheret H. (2000) *Arabidopsis* SGS2 and SGS3 genes are required for posttranscriptional gene silencing and natural virus resistance. Cell. 26; 101(5):533-42.

Navarro L, Dunoyer P, Jay F, Arnold B, Dharmasiri N, Estelle M, Voinnet O, Jones J D. (2006). A plant miRNA contributes to antibacterial resistance by repressing auxin signaling. Science. 312(5772):436-9.

Navarro L, Jay F, Nomura K, He S Y, Voinnet O. (2008). Suppression of the microRNA pathway by bacterial effector proteins. Science. 321(5891):964-7.

Nikovics K, Blein T, Peaucelle A, Ishida T, Morin H, Aida M, Laufs P. (2006) The balance between the MIR164A and CUC2 genes controls leaf margin serration in *Arabidopsis*. Plant Cell 18(11):2929-45.

Okumoto S, Schmidt R, Tegeder M, Fischer W N, Rentsch D, Frommer W B, Koch W. (2002) High affinity amino acid transporters specifically expressed in xylem parenchyma and developing seeds of *Arabidopsis*. J Biol Chem. 277(47):45338-46.

Pumplin N, Voinnet O. (2013) RNA silencing suppression by plant pathogens: defence, counter-defence and counter-counter-defence. Nat Rev Microbiol. 11(11):745-60

Qiao Y, Liu L, Xiong Q, Flores C, Wong J, Shi J, Wang X, Liu X, Xiang Q, Jiang S, Zhang F, Wang Y, Judelson H S, Chen X, Ma W. (2013) Oomycete pathogens encode RNA silencing suppressors. Nat Genet. 45(3):330-3.

Qu F, Ye X, Morris T J. (2008) *Arabidopsis* DRB4, AGO1, AGO7, and RDR6 participate in a DCL4-initiated antiviral RNA silencing pathway negatively regulated by DCL1. Proc Natl Acad Sci USA. 2008 Sep. 23; 105(38): 14732-7.

Schwach F, Vaistij F E, Jones L, Baulcombe D C. (2005) An RNA-dependent RNA polymerase prevents meristem invasion by potato virus X and is required for the activity but not the production of a systemic silencing signal. Plant Physiol. 138(4):1842-52.

Smith L M, Pontes O, Searle I, Yelina N, Yousafzai F K, Herr A J, Pikaard C S, Baulcombe D C. (2007) An SNF2 protein associated with nuclear RNA silencing and the spread of a silencing signal between cells in *Arabidopsis*. Plant Cell. (5):1507-21

Susek R. E., Ausubel F. M., Chory J. (1993). Signal transduction mutants of *Arabidopsis* uncouple nuclear CAB and RBCS gene expression from chloroplast development. Cell 74, 787-799.

Thomma B P, VAN Esse H P, Crous P W, DE Wit P J. (2005) *Cladosporium fulvum* (syn. *Passalora fulva*), a highly specialized plant pathogen as a model for functional studies on plant pathogenic Mycosphaerellaceae. Mol Plant Pathol. 2005 1; 6(4):379-93 Weiberg et al., 2014)

Xie Z, Johansen L K, Gustafson A M, Kasschau K D, Lellis A D, Zilberman D, Jacobsen S E, Carrington J C. (2004) Genetic and functional diversification of small RNA pathways in plants. PLoS Biol. 2004 2(5)

Xie Z, Allen E, Wilken A, Carrington J C (2005) DICER-LIKE 4 functions in trans-acting small interfering RNA biogenesis and vegetative phase change in *Arabidopsis thaliana*. Proc Natl Acad Sci USA 102, 12984 (2005).

Xin X F, He S Y. (2013) *Pseudomonas syringae* pv. tomato DC3000: a model pathogen for probing disease susceptibility and hormone signaling in plants. Annu Rev Phytopathol. 51:473-98.

Yang Y, Costa A, Leonhardt N, Siegel R S, Schroeder H. (2008) Isolation of a strong *Arabidopsis* guard cell promoter and its potential as a research tool. Plant Methods. 19; 4:6

Yu A, Lepère G, Jay F, Wang J, Bapaume L, Wang Y, Abraham A L, Penterman J, Fischer R L, Voinnet O, Navarro L. (2013) Dynamics and biological relevance of DNA demethylation in *Arabidopsis* antibacterial defense. Proc Natl Acad Sci USA. 110(6):2389-94.

Yu B, Yang Z, Li J, Minakhina S, Yang M, Padgett R W, Steward R, Chen X. (2005) Methylation as a crucial step in plant microRNA biogenesis. Science. 11; 307(5711): 932-5.

Weiberg A, Wang M, Bellinger M and Jin H (2014) Small RNAs: A New Paradigm in Plant-Microbe Interactions. Annu. Rev. Phytopathol. 2014. 52:495-516

Zhao H, Wang X, Zhu D, Cui S, Li X, Cao Y, Ma L. (2012) A single amino acid substitution in IIIf subfamily of basic helix-loop-helix transcription factor AtMYC1 leads to trichome and root hair patterning defects by abolishing its interaction with partner proteins in *Arabidopsis*. J Biol Chem. 20; 287(17):14109-21

The invention claimed is:

1. A method for characterizing the mode of action of natural or synthetic molecules that are known to enhance plant disease resistance comprising the following steps:
   (a) providing several types of visual PTGS reporter plants transgenic for an inverted-repeat construct which triggers post-transcriptional gene silencing of an endogenous visual reporter gene, each type driven by a different tissue-specific promoter wherein said tissue is relevant for pathogen entry and/or propagation,
   (b) applying said molecules on said plants, and (c) characterizing the mode of action of said molecules by visually observing plant changes translating an increase or decrease of said post-transcriptional gene silencing activity of said endogenous visual reporter gene in one or several of said types of visual PTGS reporter plants.

2. The method of claim 1, for characterizing the mode of action of said molecules that have a tissue-specific effect or an effect on different tissues that are relevant for pathogen entry, propagation or replication, further comprising an additional step:
  (d) comparing the visual effect between said types of visual PTGS reporter plants
    (i) wherein a tissue-specific effect means that said molecules are relevant for pathogen entry, propagation or replication only by said tissue or
    (ii) wherein an effect on different tissues means that said molecules are relevant for pathogen entry, propagation or replication by different tissues.

3. The method of claim 1, wherein said endogenous visual reporter gene is SUL cDNA of SEQ ID NO:1.

4. The method of claim 1, wherein said relevant tissue for pathogen entry and/or propagation is selected from the group consisting of hydathodes, guard cells, xylem parenchyma and cambium cells, xylem parenchyma cells, cells at the base of trichomes, mesophyll cells and epidermal cells.

5. The method of claim 1, wherein said tissue-specific promoter comprises AAP6 promoter of SEQ ID NO: 4, IRX3 promoter of SEQ ID NO: 5, GC1 promoter of SEQ ID NO: 6, HYD promoter of SEQ ID NO: 7, AHA3 promoter of SEQ ID NO: 8, MYC1 promoter of SEQ ID NO: 9, MYB60-promoter of SEQ ID NO: 10, CAB3 promoter of SEQ ID NO: 11, WOX4 promoter of SEQ ID NO: 12, and BDG promoter of SEQ ID NO: 37.

* * * * *

SEQUENCE LISTING

```
<160> NUMBER OF SEQ ID NOS: 39

<210> SEQ ID NO 1
<211> LENGTH: 1608
<212> TYPE: DNA
<213> ORGANISM: Arabidopsis thaliana
<220> FEATURE:
<221> NAME/KEY: misc_feature
<223> OTHER INFORMATION: SUL cDNA

<400> SEQUENCE: 1
tatctcctta tcctgaccac agaaacaaac ataagccaat ggaaacaaaa aaattctaag      60
gtgaaaaaag ccaatcagaa gctgagtaaa ctctaagctc acacaaaaat ggcgtctctt     120
cttggaacat cttcttctgc aatctgggct tctccttcac tctcttctcc ttcctcaaaa     180
ccttcctcct cccccatttg cttcaggcca ggaaaattgt ttggaagcaa gttaaatgca     240
ggaatccaaa taaggccaaa gaagaacagg tctcgttacc atgtttcggt tatgaatgta     300
gccactgaaa tcaactctac tgaacaagta gtagggaagt ttgattcaaa gaagagtgcg     360
agaccggttt atccatttgc agctatagta gggcaagatg agatgaagtt atgtcttttg     420
ttgaatgtta ttgatccaaa gattggtggt gttatgatta tgggagatag aggaactgga     480
aaatctacaa ctgttagatc attagttgat ctgttacctg agattaatgt agttgcaggt     540
gacccgtata actcggatcc gatagatcct gagtttatgg gtgttgaagt aagagagaga     600
gttgagaaag gagagcaagt tcctgttatt gcgactaaga ttaatatggt tgatcttcct     660
ttgggtgcaa cagaagatag agtttgtgga accatcgata tcgaaaaggc tttgacagaa     720
ggtgtaaaag cctttgagcc tggtttgttg gctaaagcta atagagggat tctttatgtt     780
gatgaagtta atctcttgga tgatcatttg gttgatgttc ttttggattc agctgcttct     840
ggttggaata cggttgagag agaagggatt tcgatttctc acccggcgag gtttatcttg     900
atcggttcag gaaatccgga agaaggagag cttaggccaa agcttcttga tcggtttggt     960
atgcatgcac aagtagggac ggttagagat gctgatttac gggtcaagat tgttgaagag    1020
agagctcgtt tcgatagtaa cccaaaggat ttccgtgaca cttacaaaac cgagcaggac    1080
aagcttcaag accagatttc aactgctagg gcaaaccttt cctcggttca gattgatagg    1140
gaattgaagg tgaagatctc tagagtttgt tcagagctca atgttgatgg ttgagagga     1200 gacatagtga ctaacagagc agcaaaagca cttgcagctc tcaaaggaaa agatcgagta    1260
actccagatg atgttgcaac cgttatccct aactgcttaa ggcaccgtct gaggaaagat    1320
ccactggaat ctattgattc aggagttcta gtttccgaga gttcgccga gattttcagc     1380 tgaataggag attcgattct gtgatcattt ttctttaact ttttctactc tgtaaacggt    1440
gagaagaacc aaaactataa acaggcaaat ctgattgaat atagagtcta tgctttattc    1500
attaagttga gttgttcaaa cttcaaatca tagactcaat agaactctgt ttatatttgt    1560
gtaactacat acaaacattc ctgcattgat tatggctata aagctatc                 1608
```

```
<210> SEQ ID NO 2
<211> LENGTH: 2351
<212> TYPE: DNA
<213> ORGANISM: Artificial
<220> FEATURE:
<223> OTHER INFORMATION: SUL-intron-LUS
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t

<400> SEQUENCE: 2
```

| | | | | | |
|---|---|---|---|---|---|
| aggatgatct | ggacgaagag | catcaggggc | tcgcgccagc | cgaactgttc | gccaggctca | 60 |
| aggcgcgcat | gcccgacggc | gatgatctcg | tcgtgaccca | tggatatcga | aaaggctttg | 120 |
| acagaaggtg | taaaagcctt | tgagcctggt | tgttggcta | aagctaatag | agggattctt | 180 |
| tatgttgatg | aagttaatct | cttggatgat | catttggttg | atgttctttt | ggattcagct | 240 |
| gcttctggtt | ggaatacggt | tgagagagaa | gggatttcga | tttctcaccc | ggcgaggttt | 300 |
| atcttgatcg | gttcaggaaa | tccggaagaa | ggagagctta | ggccacagct | tcttgatcgg | 360 |
| tttggtatgc | atgcacaagt | agggacggtt | agagatgctg | atttacgggt | caagattgtt | 420 |
| gaagagagag | ctcgtttcga | tagtaaccca | aaggatttcc | gtgacactta | caaaaccgag | 480 |
| caggacaagc | ttcaagacca | gattggcgcg | cccaatcgat | gatttaaatg | tgtaagaatt | 540 |
| tcttatgtta | cattattaca | ttcaacgttt | tatcttaatt | ggctcttcat | ttgattgaaa | 600 |
| tttgacaatt | atttcttgtt | ttttttttg  | tcacactctt | tttggggttgg | ggtggccgac | 660 |
| gaattgtggg | aaggtagaaa | gaggggagga | cttttgttat | actccattag | taattactgt | 720 |
| ttccgtttca | atttatgtga | caatatttcc | tttttagtcg | gttccaaaag | aaaatgtcag | 780 |
| cattataaac | aatttaattt | tgaaattaca | attttgccat | taataaaatg | atttacaacc | 840 |
| acaaaagtat | ctatgagcct | gtttgggtgg | gcttataagc | agcttatttt | aagtggctta | 900 |
| taagtcaaaa | agtgacantt | tttgagaagt | tagaaaatcc | taacttctca | aaaagtagct | 960 |
| tttaagccac | ttatgactta | taagtccaaa | aattttaag  | ttaccaaaca | tatattaatg | 1020 |
| ggtttataag | cttataagcc | actttttaagc | tcacccaaac | gggttctatg | tctcacttta | 1080 |
| gactacaaat | tttaaaagtc | ttcatttatt | tcttaatctc | cgtggcgagt | naaactataa | 1140 |
| cacataaagt | gaaacggagg | gaataagatg | gagtcataaa | ctaatccaaa | tctatactct | 1200 |
| ctccgttaat | ttgttttta  | gtttgatttg | gtacattaat | aaaacagatt | tttcgaaggt | 1260 |
| tataaacaca | gacagatgtt | tcccagcgag | ctagcaaaat | tccaagatttt | ctgtcgaaaa | 1320 |
| ttcgtgtgtt | tctagctagt | acttgatgtt | atctttaacc | ttttagtaat | tttttgtcct | 1380 |
| tttctttcta | tttttcatct | tacaatgaat | tatgagcaag | ttccttaagt | agcatcacac | 1440 |
| gtgagatgtt | ttttatgata | ttgactaaat | ccaatctta  | ccattcctta | actagtaaaa | 1500 |
| tacaacacat | gttaattgat | acattgctta | acactgaggt | tagaaaattt | tagaaattag | 1560 |
| ttgtccaaat | gctttgaaat | tagaaatctt | taatccctta | ttttttttta | aaatgttttt | 1620 |
| tctcactcca | aagaaagaga | aactgacatg | aaagctcaaa | agatcatgaa | tcttactaac | 1680 |
| tttgtggaac | taaatgtaca | tcagaatgtt | tctgacatgt | gaaaatgaaa | gctcttaatt | 1740 |
| ttcttctttt | atttattgag | ggttttttgca | tgctatgcat | tcaatttgag | tactttaaag | 1800 |
| cacctataaa | cacttactta | cacttgcctt | ggagtttatg | ttttagtgtt | ttcttcacaa | 1860 |

```
agcttgtcct gctcggtttt gtaagtgtca cggaaatcct ttgggttact atcgaaacga      1920
gctctctctt caacaatctt gacccgtaaa tcagcatctc taaccgtccc tacttgtgca      1980
tgcataccaa accgatcaag aagctgtggc ctaagctctc cttcttccgg atttcctgaa      2040
ccgatcaaga taaacctcgc cgggtgagaa atcgaaatcc cttctctctc aaccgtattc      2100
caaccagaag cagctgaatc caaaagaaca tcaaccaaat gatcatccaa gagattaact      2160
tcatcaacat aaagaatccc tctattagct ttagccaaca aaccaggctc aaaggctttt      2220
acaccttctg tcaaagcctt ttcgatatcc atggcgatgc ctgcttgccg aatatcatgg      2280
tggaaaatgg ccgcttttct ggattcatcg actgtggccg ctgggtgtg gcggaccgct       2340 atcaggacat a                                                           2351

<210> SEQ ID NO 3
<211> LENGTH: 4979
<212> TYPE: DNA
<213> ORGANISM: Artificial
<220> FEATURE:
<223> OTHER INFORMATION: AAP6 promoter-CAACTTTGTATACAAAAGTTG-SUL-intron-
      LUS
<220> FEATURE:
<221> NAME/KEY: misc_feature
<222> LOCATION: (3546)..(3546)
<223> OTHER INFORMATION: n is a, c, g, or t
<220> FEATURE:
<221> NAME/KEY: misc_feature
<222> LOCATION: (3759)..(3759)
<223> OTHER INFORMATION: n is a, c, g, or t

<400> SEQUENCE: 3
gctgatgctg ttattaattt gtgtcgcatc aattaattaa aactgatgca aatctaagtt        60
agtttgtatc acttttacat attgatataa atatataaat ttacatcact taaataactg       120
atatgtttat taatttaatt aacatcactt aaaaaatgat atatatttta catcaataaa       180
aaagtgatgc caataaataa tttatcaact acatcatttt ttttttatcg attcttaagt       240
taatttaatt agcatcattt cttttatgat tttacatcac ttcattttt ttaattgcca        300 tctttaataa cttttgtagt ctaatattct tttggaaaca gaatatccat ttactttttt      360
ccccacgatt atgaaatctt cctagaatcc taacttccct aatatctcta taaatctacg      420
tttcctttgc taatatgata gattttttctt tttcttttta atataacttc ttcttctttt    480
catcatctct tcttccctag aagaacaaaa caccaaaata atgaaacaaa actatgtcg       540 ccaaaggtaa accgaaccta cgttcgtgta atcggttaag aagtcggaga cacaagttct     600
ttcggtctct cccctaatta agaaaaccag ggaagatatc gcaagaaaac gccaacggtg     660
tacaatcttc agggtaaaat catgagaagc cacaaagaga tcatgagaag gttaaaaaca    720
ttaagcacaa tgaaaacatt ttttgatgc ttagatatct tgtaaggaag atgaccgtga      780
ggaaaattat ggagacatat gtggtatgtc tctgtgtgat tacaagagaa tcaaagaaca    840
aaagtagttt atagtttga agtttaattt gtagtattt acttttgaac tatgtacgtg       900
gtttaatttc ttcaatgaat ttaagatttt ttgtattatt ttatttataa ttagtgatta    960
ttgaaaataa acaattatt aaaaaatatt tatgaaaact aaaattaatt caatcggtta     1020
ttcagtattt gacaaaaaaa aattaacatc cattatttta aatgatacaa ttatttgaat    1080
catttattaa aactgacatt aatctttaca tcagtaatt acaatcaata caaatattta     1140
acatcactta caataatcga aacaaatact aacatcattt ttattaatcg atgcaaaatt   1200
aacatcatct atttgcaaat gatacataat aacatcggtt ataataatcg atgcaaatat  1260
```

```
ttattttaaa tgatgtaaat tatttacatc aacagtatat aaatcattta tttaaatgat    1320 gtaatttttct tttacatcaa ttataagtaa tacaaatatt taaaataaat gatataaaat   1380
gatcactttt ttgtagtgac tggctaaacc gatgaaaaca aatatgaatt gaaatcaaag    1440
aaataatgtt atcttgtgta acaagacttt gaaaacttaa ttagcttatt ctcttttaac   1500
tttggtataa ataaacaact tttatatttg ctatgaaata taccaaaaac gggctttgta   1560
attggtcgac tctcttatca gaatttgatg tcaagaccgc gtgataaaac atcaagaaca   1620
tggtctaaca tagtggaaag aaaaaaatat ttgatagtaa tagaatcgtt gaaaattcaa   1680
ctatcgtcaa ccttattcaa caggaatata aaacgaaaaa ccgtaattgg ctcgaagttt   1740
ggttgaaaaa tcaaaagcca aaatctatga acgagattaa tcgcccacta aagtcccttc   1800
tgttattggc acacgctctt gtcgttatag ttaaaaagtt cttcaaatac agagacattt   1860
tgtttatgta ctacatacga ttcggtttgg tgaacaaaat atcataaaac ttggttcatg   1920
ttgatatata gattcataag atgtattttt gtcttatata tgtttctgta tcatgggtta   1980
aaatgtttta caaatatgtt ttttttttta aaatatgtat ttatgtatat atgaatccgt   2040
acgcgtagta gtaaaatgaa ttagaaagga ataggaattg aaaatttcat attatgtgta   2100
tgtgtggaat caagaaatga ataaaatgat aagtggtgga ccttgtaacc taagatccag   2160
gaaactacag aggagagcca ctgatagtgt gtcaataatt attctcccac ccatccacaa   2220
agaaaagtta atttaattta tcactctcag taaattataa tcaaaataaa caccaacagt   2280
agtcaacttt caacaaatgg gtctgagcct atccaatata tataatcgat cgaagcaatc   2340
tattcgacat taatgaatct cattcataaa atcataacgt aaaataataa atatattaat   2400
tacagagaca gacaataatg aaaggtgtga aaaatgaaca ctacaatata aaagatgaca   2460
tttaaaataa aataaaagag agaaagggat taggtgtgaa atgtggtgtg tctatttaag   2520
tggagaagag tccttgacac tccatacata ctacctttgg cctcttcttc ttatttatc    2580 atagctaagc tcaaaaacaa tcgatagcaa ctttgtatac aaaagttgag gatgatctgg   2640
acgaagagca tcaggggctc gcgccagccg aactgttcgc caggctcaag gcgcgcatgc   2700
ccgacggcga tgatctcgtc gtgacccatg gatatcgaaa aggctttgac agaaggtgta   2760
aaagcctttg agcctggttt gttggctaaa gctaatagag ggattcttta tgttgatgaa   2820
gttaatctct tggatgatca tttggttgat gttcttttgg attcagctgc ttctggttgg   2880
aatacggttg agagagaagg gatttcgatt tctcacccgg cgaggtttat cttgatcggt   2940
tcaggaaatc cggaagaagg agagcttagg ccacagcttc ttgatcggtt tggtatgcat   3000
gcacaagtag ggacggttag agatgctgat ttacgggtca agattgttga agagagagct   3060
cgtttcgata gtaacccaaa ggatttccgt gacacttaca aaaccgagca ggacaagctt   3120
caagaccaga ttggcgcgcc caatcgatga tttaaatgtg taagaatttc ttatgttaca   3180
ttattacatt caacgtttta tcttaattgg ctcttcattt gattgaaatt tgacaattat   3240
ttcttgtttt ttttttttgtc acactctttt tgggttgggg tggccgacga attgtgggaa   3300
ggtagaaaga ggggaggact tttgttatac tccattagta attactgttt ccgtttcaat   3360
ttatgtgaca atatttcctt tttagtcggt tccaaaagaa aatgtcagca ttataaacaa   3420
tttaattttg aaattacaat tttgccatta ataaaatgat ttacaaccac aaaagtatct   3480
atgagcctgt ttgggtgggc ttataagcag cttattttaa gtggcttata agtcaaaaag   3540
tgacantttt tgagaagtta gaaaatccta acttctcaaa aagtagcttt taagccactt   3600
```

```
atgacttata agtccaaaaa tttttaagtt accaaacata tattaatggg tttataagct    3660
tataagccac ttttaagctc acccaaacgg gttctatgtc tcactttaga ctacaaattt    3720
taaaagtctt catttatttc ttaatctccg tggcgagtna actataaca cataaagtga    3780 aacggaggga ataagatgga gtcataaact aatccaaatc tatactctct ccgttaattt    3840
gttttttagt ttgatttggt acattaataa aacagatttt tcgaaggtta taaacacaga    3900
cagatgtttc ccagcgagct agcaaaaattc caagatttct gtcgaaaatt cgtgtgtttc    3960
tagctagtac ttgatgttat ctttaacctt ttagtaattt tttgtccttt tctttctatt    4020
tttcatctta caatgaatta tgagcaagtt ccttaagtag catcacacgt gagatgtttt    4080
ttatgatatt gactaaatcc aatctttacc attccttaac tagtaaaata caacacatgt    4140
taattgatac attgcttaac actgaggtta gaaaatttta gaaattagtt gtccaaatgc    4200
tttgaaatta gaaatcttta atcccttatt ttttttttaaa atgttttttc tcactccaaa    4260
gaaagagaaa ctgacatgaa agctcaaaag atcatgaatc ttactaactt tgtggaacta    4320
aatgtacatc agaatgtttc tgacatgtga aaatgaaagc tcttaatttt cttcttttat    4380
ttattgaggg ttttttgcatg ctatgcattc aatttgagta ctttaaagca cctataaaca    4440
cttacttaca cttgccttgg agtttatgtt ttagtgtttt cttcacaaag cttgtcctgc    4500
tcggttttgt aagtgtcacg gaaatccttt gggttactat cgaaacgagc tctctcttca    4560
acaatcttga cccgtaaatc agcatctcta accgtcccta cttgtgcatg cataccaaac    4620
cgatcaagaa gctgtggcct aagctctcct tcttccggat ttcctgaacc gatcaagata    4680
aacctcgccg ggtgagaaat cgaaatccct tctctctcaa ccgtattcca accagaagca    4740
gctgaatcca aaagaacatc aaccaaatga tcatccaaga gattaacttc atcaacataa    4800
agaatccctc tattagcttt agccaacaaa ccaggctcaa aggcttttac accttctgtc    4860
aaagcctttt cgatatccat ggcgatgcct gcttgccgaa tatcatggtg gaaaatggcc    4920
gcttttctgg attcatcgac tgtggccggc tgggtgtggc ggaccgctat caggacata    4979
```

<210> SEQ ID NO 4  
<211> LENGTH: 2607  
<212> TYPE: DNA  
<213> ORGANISM: Artificial  
<220> FEATURE:  
<223> OTHER INFORMATION: AAP6 promoter

<400> SEQUENCE: 4

```
gctgatgctg ttattaattt gtgtcgcatc aattaattaa aactgatgca aatctaagtt      60
agtttgtatc acttttacat attgatataa atatataaat ttacatcact taaataactg     120
atatgtttat taatttaatt aacatcactt aaaaaatgat atatatttta catcaataaa     180
aaagtgatgc caataaataa tttatcaact acatcatttt ttttttatcg attcttaagt     240
taatttaatt agcatcattt cttttatgat tttacatcac ttcattttt ttaattgcca     300 tctttaataa cttttgtagt ctaatattct tttggaaaca gaatatccat ttacttttt     360 ccccacgatt atgaaatctt cctagaatcc taacttccct aatatctcta taaatctacg     420
tttcctttgc taatatgata gatttttctt tttcttttta atataacttc ttcttctttt     480
catcatctct tcttccctag aagaacaaaa caccaaaata atgaaacaaa aactatgtcg     540
ccaaaggtaa accgaaccta cgttcgtgta atcggttaag aagtcggaga cacaagttct     600
ttcggtctct cccctaatta agaaaaccag ggaagatatc gcaagaaaac gccaacggtg     660
tacaatcttc agggtaaaat catgagaagc cacaaagaga tcatgagaag gttaaaaaca     720
```

```
ttaagcacaa tgaaaacatt tttttgatgc ttagatatct tgtaaggaag atgaccgtga      780
ggaaaattat ggagacatat gtggtatgtc tctgtgtgat tacaagagaa tcaaagaaca      840
aaagtagttt atagttttga agtttaattt gtagtatttt acttttgaac tatgtacgtg      900
gtttaatttc ttcaatgaat ttaagatttt ttgtattatt ttatttataa ttagtgatta      960
ttgaaaataa aacaattatt aaaaaatatt tatgaaaact aaaattaatt caatcggtta     1020
ttcagtattt gacaaaaaaa aattaacatc cattattttta aatgatacaa ttatttgaat     1080
catttattaa aactgacatt aatctttaca tcagtaattt acaatcaata caaatatttta     1140 acatcactta caataatcga aacaaatact aacatcattt ttattaatcg atgcaaaatt     1200
aacatcatct atttgcaaat gatacataat aacatcggtt ataataatcg atgcaaatat     1260
ttattttaaa tgatgtaaat tatttacatc aacagtatat aaatcattta tttaaatgat     1320
gtaattttct tttacatcaa ttataagtaa tacaaatatt taaaataaat gatataaaat     1380
gatcactttt ttgtagtgac tggctaaacc gatgaaaaca aatatgaatt gaaatcaaag     1440
aaataatgtt atcttgtgta acaagacttt gaaaacttaa ttagcttatt ctcttttaac     1500
tttggtataa ataaacaact tttatatttg ctatgaaata taccaaaaac gggctttgta     1560
attggtcgac tctcttatca gaatttgatg tcaagaccgc gtgataaaac atcaagaaca     1620
tggtctaaca tagtggaaag aaaaaaatat ttgatagtaa tagaatcgtt gaaaattcaa     1680
ctatcgtcaa ccttattcaa caggaatata aaacgaaaaa ccgtaattgg ctcgaagttt     1740
ggttgaaaaa tcaaaagcca aaatctatga acgagattaa tcgcccacta aagtcccttc     1800
tgttattggc acacgctctt gtcgttatag ttaaaaagtt cttcaaatac agagacattt     1860
tgtttatgta ctacatacga ttcggtttgg tgaacaaaat atcataaaac ttggttcatg     1920
ttgatatata gattcataag atgtattttt gtcttatata tgtttctgta tcatgggtta     1980
aaatgtttta caaatatgtt ttttttttta aaatatgtat ttatgtatat atgaatccgt     2040
acgcgtagta gtaaaatgaa ttagaaagga ataggaattg aaaatttcat attatgtgta     2100
tgtgtggaat caagaaatga ataaaatgat aagtggtgga ccttgtaacc taagatccag     2160
gaaactacag aggagagcca ctgatagtgt gtcaataatt attctcccac ccatccacaa     2220
agaaaagtta atttaattta tcactctcag taaattataa tcaaaataaa caccaacagt     2280
agtcaacttt caacaaatgg gtctgagcct atccaatata tataatcgat cgaagcaatc     2340
tattcgacat taatgaatct cattcataaa atcataacgt aaaataataa atatattaat     2400
tacagagaca gacaataatg aaaggtgtga aaaatgaaca ctacaatata aaagatgaca     2460
tttaaaataa aataaagag agaaagggat taggtgtgaa atgtggtgtg tctatttaag     2520
tggagaagag tccttgacac tccatacata ctacctttgg cctcttcttc ttatttatc     2580 atagctaagc tcaaaaacaa tcgatag                                         2607
```

<210> SEQ ID NO 5
<211> LENGTH: 1133
<212> TYPE: DNA
<213> ORGANISM: Artificial
<220> FEATURE:
<223> OTHER INFORMATION: IRX3 promoter
<400> SEQUENCE: 5

```
aaaataagta aaagatcttt tagttgtttg ctttgtatgt tgcgaacagt ttgattctgt       60
ttttcttttt ccttttttg ggtaatttc ttataactt tttcatagtt tcgattatt         120
```

```
ggataaaatt ttcagattga ggatcatttt atttatttat tagtgtagtc taatttagtt      180
gtataactat aaaattgttg tttgtttccg aatcataagt tttttttttt tttggttttg      240
tattgatagg tgcaagagac tcaaaattct ggtttcgatg ttaacagaat tcaagtagct      300
gcccacttga ttcgatttgt tttgtatttg gaaacaacca tggctggtca aggcccagcc      360
cgttgtgctt ctgaacctgc ctagtcccat ggactagatc tttatccgca gactccaaaa      420
gaaaaaggat tggcgcagag gaattgtcat ggaaacagaa tgaacaagaa agggtgaaga      480
agatcaaagg catatatgat ctttacattc tctttagctt atgtatgcag aaaattcacc      540
taattaagga cagggaacgt aacttggctt gcactcctct caccaaacct taccccctaa      600
ctaattttaa ttcaaaatta ctagtatttt ggccgatcac tttatataat aagataccag      660
atttattata tttacgaatt atcagcatgc atatactgta tatagttttt tttttgttaa      720
agggtaaaat aataggatcc ttttgaataa aatgaacata taattagt ataatgaaaa      780 cagaaggaaa tgagattagg acagtaagta aaatgagaga gacctgcaaa ggataaaaaa      840
gagaagctta aggaaaccgc gacgatgaaa gaaagacatg tcatcagctg atggatgtga      900
gtgatgagtt tgttgcagtt gtgtagaaat ttttactaaa acagttgttt ttacaaaaaa      960
gaaataatat aaaacgaaag cttagcttga aggcaatgga gactctacaa caaactatgt     1020
accatacaga gagagaaact aaaagctttt cacacataaa aaccaaactt attcgtctct     1080
cattgatcac cgttttgttc tctcaagatc gctgctaatc tccggccgtc cct            1133

<210> SEQ ID NO 6
<211> LENGTH: 1627
<212> TYPE: DNA
<213> ORGANISM: Artificial
<220> FEATURE:
<223> OTHER INFORMATION: GC1 promoter

<400> SEQUENCE: 6
tttggaacac tctaccaacg ccgccatgaa aggatctctc atggccgcag gggacgtgtt       60
cttcttacat ctggtgttag ggctatggtt actccagtga ggagggagag gcaagaggtt      120
gcttaatgat tcgttttttcc ggtgatacga gaactcttta ggtttaccgg gaagcttttc      180
ccatgaaaat gggatgccaa gtggatggag aggagttgcc ggagagttgc cggagaatag      240
gagggaattg gaggaggagg aagagagtga tcgccgggtt gaaatgttaa ccgtcgagga      300
gaatttgacc gagttggatc gtctagtagg tacaattcgg gtccttggcg aagtatccat      360
tcaaaatagt gtttagtttt ggacttgaga acttgttgtc tctttgatct cttttatata      420
aaactttgga cgtgtaggac aaacttgtca acataagaaa caaaatggtt gcaacagaga      480
ggatgaattt ataagttttc aacaccgctt ttcttattag acggacaaca atctatagtg      540
gagtaaattt ttatttttgg taaaatggtt agtgaattca aatatctaaa ttttgtgact      600
cactaacatt aacaaatatg cataagacat aaaaaaaaga aagaataatt cttatgaaac      660
aagaaaaaaa acctatacaa tcaatcttta ggaattgacg atgtagaatt gtagatgata      720
aattttctca aatatagatg ggcctaatga agggtgccgc ttattggatc tgacccattt      780
tgaggacatt aatattttca ttggttataa gccttttaat caaaattgtc attaaattga      840
tgtctccctc tcgggtcatt ttcctttctc cctcacaatt aatgtagact ttagcaattt      900
gcacgctgtg ctttgtcttt atatttagta acacaaacat tttgacttgt cttgtagagt      960
ttttctcttt tattttctta tccaaatgaa aaactaaaag tgttctcgta tacatatatt     1020
aaaattaaag aaacctatga aaacaccaat acaaatgcga tattgttttc agttcgacgt     1080
```

-continued

```
ttcatgtttg ttagaaaatt tctaatgacg tttgtataaa atagacaatt aaacgccaaa    1140
cactacatct gtgttttcga acaatattgc gtctgcgttt ccttcatcta tctctctcag    1200
tgtcacaatg tctgaactaa gagacagctg taaactatca ttaagacata aactaccaaa    1260
gtatcaagct aatgtaaaaa ttactctcat ttccacgtaa caaattgagt tagcttaaga    1320
tattagtgaa actaggtttg aatttcttc ttcttcttcc atgcatcctc cgaaaaaagg    1380
gaaccaatca aaactgtttg catatcaaac tccaacactt tacagcaaat gcaatctata    1440
atctgtgatt tatccaataa aaacctgtga tttatgtttg gctccagcga tgaaagtcta    1500
tgcatgtgat ctctatccaa catgagtaat tgttcagaaa ataaaaagta gctgaaatgt    1560
atctatataa agaatcatcc acaagtacta ttttcacaca ctacttcaaa atcactactc    1620
aagaaat                                                              1627
```

<210> SEQ ID NO 7
<211> LENGTH: 951
<212> TYPE: DNA
<213> ORGANISM: Artificial
<220> FEATURE:
<223> OTHER INFORMATION: HYD promoter

<400> SEQUENCE: 7

```
aagttaggac aacacgcaaa gccctacgtg cactctttca ttattcctct cttcttttgc     60
ccccaacagt ctttgacgac ccaccttgcc cttttgaccc ttctctctca cgcacatgta    120
tgttattaat tcaaatggtt cttttatgct tcggcattta tcatcatgat atacatacat    180
atcgatcgat agaggaaaaa aaaaaatcat ttatgtagta gaaaatttac agatatatat    240
atatatatat atatatcgta taatgtatat caatatttga atttgaagag tttcaatata    300
aactgaaaca aagttaagtg tagattatta ttagtgagga actagtggat atccagttta    360
ttttggtata taccggtaat tcattctaat gaagtgaaag aatatggata ctgtatttt    420 ttaccatgcc atagagtaga tgctagctaa agattagtcg taagagaggt ctaaggtctt    480
gcttgtcaac gcgtgaccgg cttcatagga tcctagcaat aagacaatat ggtacgccta    540
gcaacctagc acttatatat gtagagtttg tgaaatttag ggcagacaag cccccacact    600
aaaaaaacag taatatggaa taaaaaaaag ctttcaaaac ttagcagtta ttagacaagg    660
tattgtttgg ccctagctag cgatcgttta gctctcttca ctctctcact ttttagttc    720 aacccttctt ttgcgtgaga tgccatcatg gcatggtatg gttcttttgc cttacgtaaa    780
acacactcac gccagcacac acacacacac acataacata tacggatgtg cgtgtgagct    840
agtcttccat taatgcaatc tttgggccta tatatacaaa cctttccata accaaagttc    900
tcatactaca aacgccctc atgtgcttgg aaatgcgggt gagaatctcc a              951
```

<210> SEQ ID NO 8
<211> LENGTH: 2792
<212> TYPE: DNA
<213> ORGANISM: Artificial
<220> FEATURE:
<223> OTHER INFORMATION: AHA3 promoter

<400> SEQUENCE: 8

```
aataactacg tatatgctgg gaagatataa agaaaaacct acatagagaa tacgaacatg     60
aatatcacaa taagcgttgg tccaacgacc ttccaacaag cacctcttgt atgattcgac    120
ttctacattt attcatcacc tctctttttt ctcttgttta ttagattctt attatcatgt    180
```

```
gttttgtttc ccccttttatt attattatct cttagaacct tgttcgttca tgaaaatcta      240
ttatcaacaa aactgaattg aaaataaaaa gaatgattca agatgaaagt aaattcacta      300
aaagaaattt accaaaaaaa aaaagtatac ttgttaaaaa aagagattga aaaagacatc      360
ttcactatat atgttgggtt cgaataaatt cgctggcctt ttctcttaag ccacatggta      420
tgagaattgt tttgtaaaat ttgttgtcat cttgttattg ccaatgcatc atgatcgtag      480
agatgtaggc taaagaaact ttttaaagt gtgattttac acagcagctg gtggttactg       540
cttagccata aaattatgtg ttgatattga cataagtgga atgtcgaaaa catgtttatt      600
catacacgta tattgttgaa agaagtgtta aacacatcat acgttaaaag tagacaaatc      660
tagaaatata taacaaaaga gaatttgttt gtacatttaa aaagccttag ctcttttttga     720 gcaaatatg taatattata atttcaacac ttttgagtgt gtttactaaa actaacaacc       780
tttatgaagc aattgggatg ggtttgtgtg atctaaaatt gaggtaggat cgtgggacca      840
ggagaacatg agatgcatcg aaggcaaagt ccaaagacac tacgtcactt tgagtggatt      900
gtgtacgtga ggttgtacga accatcattt cacgttacat atgttgcaac gctgcgtaat      960
ctgtccccac catccaactt atttctaatt ctttttcata attatatttg tatctaaact     1020
aagtagaata cctacatatt gaaaagaaat attacttgct agggcctagg gataaacgtt     1080
aaagagaaat attactatag agaaaaaccc tttagttttg aacacaattt ctatgtgtaa     1140
acatgcgtga ttgttatgta ggcagatgtg cactaagcac ttaaacagaa aaagagacaa     1200
gttttgaaca tgagttatga gtaaaacata taattataaa gttttgaaca tgagttatga     1260
gtaaaaacat atcattataa agttttgaga gcatctatga gtaaaaacag actaaattaa     1320
atagaacata tatatggaca atatagcaag taaaatctct cggactgacg aaatagatgt     1380
aactatacta ccaatgcttg cgattcaaac cgtcaaaagt gaaaaatact gtgaaataac     1440
aagtcaactt ctataaatga aaattaatat atattgtaga cggtttatat atacgtttgg     1500
atcatatcga ttcactaata aaaaagtaac aagtgttatt ccacaagttg cattttcat      1560 ttgtctataa gaactttatt gatcttaaat aacgtttatg cttttctta cacatatatg      1620 gaaccgaatt caacaaaaac tttcaaatag atttgtttta tatgaacaca attatgtata     1680
ttgattgtcc atttatgaag aaaagaataa tcttatgctt cacaccgttg acaaaaaaag     1740
ataaacgtat gtcattaacc ctctcttttt ctggtacatg tcagagcaaa gaaaatttac     1800
taaaaggtta ttttgttttt ccttgtttgt ctataaatct actgaaagct ttaaatgcaa     1860
ttttattatt ttcaagaatc ggtctttta cacttccgcg atactagcta aaggaatgta      1920
cacgtgtcag gatattattg tagcatctga ttttaccat tgatggtaac taaagttagt      1980
aacagaacca tcaggtccat caccgtaaaa tatgactagc acagtagcac ctttaccaga     2040
aaataacgcc gttagctgtt ttcatcaagt caacaacaac catttaacg gcagtttaga      2100 tatattttaa ttttttttaa ccatatatca ttggaagtaa aaagttgtca tactaaaata     2160
tatatctttt aagatctcaa ggtaattaaa aaaataatca aagacgctta aaatctgaaa     2220
ttttcaataa agtaatcata aattattta tgatttaaat ttaggtttat cataataatc      2280
ttgaaagaaa ttaaataata taatagtttt aaggaaatct atttatttgt ttttgataa      2340 attacatatc tatagtaaat taatgatatt gaatggtgta gttggtttct cataggtaga     2400
attaagactt tctcttttgt attaataaaa ttttatttga caacaaacag aagaaacctt     2460
ttaataaatt gagagagata tactatagga catgatatga caaaactgtc ctactcagtg     2520
aacttcacta acagagctca aatttgaaat ctcaatgaat taatatttaa tgacataaca     2580
```

| | |
|---|---|
| agtcaaagtg atgatattaa atctttcctc cttgacaaga cgataatact tcaattaaca | 2640 |
| aaaaaaaaaa aaaaaagaga tgataatttt tccagaataa aatattttcg acttggactg | 2700 |
| ggaataaaaa aaatggggtg acctaaaccg acgtcgcata gttacgagag gcatataaat | 2760 |
| agagagccac caaatagcct aacgtagtcc ac | 2792 |

<210> SEQ ID NO 9
<211> LENGTH: 2578
<212> TYPE: DNA
<213> ORGANISM: Artificial
<220> FEATURE:
<223> OTHER INFORMATION: MYC1 promoter

<400> SEQUENCE: 9

| | |
|---|---|
| gttggttcaa atcaattttg aaatcctaaa aaagttttca ggattcactc agatccgttg | 60 |
| agtacaaaag ggttttgtct tttaccactt ttttttctaat ccacgtggcg tgacctgaca | 120 |
| cgtcagataa gtacgcgcgt tgcaacttta tcaaggggct tttgtgaata ttactatggg | 180 |
| cttttcagaa tatattattg ggcctgtaaa gtcacgtcac taaaaaaagt agtttatcta | 240 |
| catcaaatgt gttttattatt taataacttt agtgtgttgt tgtacttgca cgagtgtata | 300 |
| tgaatttaga ataatactat cttaaacaat cggctaagct atttataatc tgtaagattg | 360 |
| atactaacga tgtaacatta atgtattaat ccgaagacag tcgtgcattg tagtggcaaa | 420 |
| tgttgtatgt cagatgtgtc gcgtctgtaa tcaatgcgct acgtctctct gtcttaacaa | 480 |
| aatcattgaa gctttaaatt tgaatttcat tattttacaa ttgcatttct ctcgtaagtc | 540 |
| gtaactttca tattcatttt ttgaagattt tttaaggata aatgtgaat tactattacc | 600 |
| aaaagaaaca ttgttattta ctttgggaca gcttctagat atggacccca acaaaaaaaa | 660 |
| aaaaaaaaaa aactgaaact aatacaagtc aagacccaac tatagtaact aggtttgggt | 720 |
| gaaccattgg gacaacaatc ttccacaacc tttgcgatat tgtcacggat ggttatgtca | 780 |
| atctgccaca aaacaatctt aggagagaac ttgaagtgtt gtgcaatctc tcatttcttt | 840 |
| ctctccgaag aaagaaaatt gttgcttgta taatgagaat taaagacttc aagttctcac | 900 |
| tcaactttaa atttatctaa ctttttctctt tgtcgtggtt catgtcgctt cttttttcatc | 960 |
| ctgaatgcaa tttgatatag gatcccattg gttaggattg tatatgtttt gtaaaattta | 1020 |
| gggtaatata tagactttta tactataatt ttattattat atacatttaa aaaatgtcta | 1080 |
| gggcatctaa aattaaatta attgtttcta tgaaaataga aaatataaac acaaacatat | 1140 |
| ggctataatg agtgtgttgt gccaacagaa ataatttata aaattaaaca caaagttttg | 1200 |
| tcgttatgga aataaatgtg catgcaacca caagtggtgc gttactaaat tatgtagggc | 1260 |
| ttcgtggata gagatggatc aattattatt ttcacgagtt tcttgccttc atttcagcca | 1320 |
| gctctctcct gatcttgcct tcaatttat tactattttt ttactgccac ttgctatatt | 1380 |
| tacttacttc ggacaaaata gtgctttgat ggtaaacaaa taacgatcgg tatatgcgat | 1440 |
| gtctcgcgat tgattatcaa acttgaacag tagtgtgtat ttgtttaata tataatctat | 1500 |
| tagagtatca tggaattatt cgggtgaaat gcgcatttat atctatcata gaaactagaa | 1560 |
| tcttcactat ccaaatagta tattccattt tcttgcaact acgtataact acattctgtt | 1620 |
| tgtcatatat ttaagatcga gtaacaaaaa attaatcatc ttcattgatg tgagccagac | 1680 |
| aaagagttca attttttttgg ttgttaaagt atgttgatac ttgatacgtt taccaaaaca | 1740 |
| caaaaaaaca atgtaggtcg atacgttcca tttccacaca acaagataga tacaaatata | 1800 |

```
taatgattgt aagacaataa gaccccgaca tgtcttaaca cgaaaaaaaa agtaactaag    1860
tttatataaa ccaacacaag tttaactaag aatctaagaa tctctacttt gttgatttca    1920
taagtgtatt catctaaatt agttataagt acaatgtaat atcaacatgt atttatattg    1980
tctcttgttg gatattaact atccaaacca aacctataat atgaaatcat caaaacatta    2040
atcattatgg tcaaactatc tcaagttgta ttctttaaaa agtgtcacga taaactctaa    2100
catcatagtg gatttaagac aacacaaatc caaagagtt aaaaagatcg gtcttaaatt     2160
tatgattcat atccatgcat gatgttggcc aatcacctag tatagtagta ataaccaagc    2220
ttttgactaa atgaatagga ggaaacaaaa aaactatatt gaatcttttct ttttgcaata   2280 tttttcagca tcatcactaa tttagagaat attttacctt ggttttcacc aaatagaatc    2340
caacactatt accatatgta ttgtataaag ataagtcact ccaaaaacca agatcatgac    2400
ccaagtcaac cactctctct cataattcag acacagtact caactttaaa gacactcttt    2460
taagactttc catcaggacc aagctgagaa agagaaagca ataagaaag aaagaaaagg     2520 aaataaagct tcaataccaa acccttcttt aataaattt gccttttggt tgtctcct      2578
```

```
<210> SEQ ID NO 10
<211> LENGTH: 262
<212> TYPE: DNA
<213> ORGANISM: Artificial
<220> FEATURE:
<223> OTHER INFORMATION: MYB60 promoter

<400> SEQUENCE: 10
```

```
cgtgtggaga tcaacatatc ttcgttaatt gactacgcaa aatagttaat ggaaaaggca     60
gagtgactcg tgagcttggc agatccaaaa gaggttgtca agaaaaagca gatttaaaag    120
ttcttccctc ttctttaagt cacccattaa tttcacatat atgtacatac atgttgcatt    180
taactcatat acatacatat tctcacatct ataaagagag cataagactc agagagatct    240
agaggaagag agagagagaa ag                                             262
```

```
<210> SEQ ID NO 11
<211> LENGTH: 1484
<212> TYPE: DNA
<213> ORGANISM: artificial
<220> FEATURE:
<223> OTHER INFORMATION: CAB3 promoter

<400> SEQUENCE: 11
```

```
aaatcaagag aaatgtgat tctcggatgt tagcttgaac aacacgaaag agtcttttat      60
ataagttttt tatattccct tgatttaact tgtatatcgt ctcttcacaa aatatgatcg    120
cattgaagaa gaaattgcaa tcgttttttt tcttctgatt gagagaatta gagaatagat    180
aatgaagtag tttcttccgt gtttggttga ttctgaagct cgtaacattg gctcatacga    240
tatgtggata acaatatatc acattgctct gataccatat taaaatcaca tccacgcatt    300
gaatggactg atcatatatc ttacatatta gttaaaatcc attgtcgtgc gagagattgc    360
cttccgtgac atcctctgtg gaccaggttc gcttgtcaca ctagctataa ttggtgaaca    420
catgataaca tatatgtttg gagcatagaa gagctagcgc ctgtgtcatt ggtgtgtggt    480
atcgaaagaa caagagaata gaacaggaga acatgaatat agctaggttt attcattttc    540
accccaaagc tgagaaattg cgttccaaag agtgggtgaa ttgatgtgtg agggcaatta    600
gtgattgtaa aaataaaatt gtgttttgta aaaaactttt actgtcgaaa ttatttaggg    660
tgatgaaaaa atcagtaaac tacgaatgat agcttaaaga gtttctatca aagtgattga    720
```

```
ggaatagttt gttgcaaatt aaacctctaa caaaatgttt tctgttgtgg tttttcatct    780
ctacaaattt tgaattttat gatgaattag aaagatagaa tgagttactt tagattttaa    840
aaggttgttc aagtttacaa aacagattac tagaatcatg attaaaaatt tacaagctac    900
atattgtcta aaccaatgat gttgaacata ccagatgata gttttcagt gtttgaacaa     960 tcaattggat agtttttatg tttctgcaaa atatgcaaat aatcagtgtt tttgagtctt   1020
tgcattttga tttaaaagca aaacaactg agtttcaagg ttaaattaat tacattattc    1080
atgagattta tcaggttagt ggataaactg acaatggaat caatgttatt gtaaattggt   1140
agtgatgttg gacttctaat gttactctct atgatgtttc ggtcatcaat atcacactat   1200
ctttactttt atttaaagga aagatcacac aaataagtta tctctattca gaactattaa   1260
gctgcttcca aaagacttgc aacatgtggt ctggaaatgc tttggctgca atgaaaaaat   1320
catagcaaaa gctagtggac tagagactgc cacataagaa tagtaaacgt taaaaccaaa   1380
atctcaaaaa tccaatgagt aaagagatat agattacttc atagataaca aacgttactc   1440 gcaatttcc tatataatcc aaccctacct aaccattttc aatc                     1484

<210> SEQ ID NO 12
<211> LENGTH: 2200
<212> TYPE: DNA
<213> ORGANISM: Artificial
<220> FEATURE:
<223> OTHER INFORMATION: WOX4 promoter

<400> SEQUENCE: 12
ggcaagtgta gtggaggagg gtcactgcat atgaatatcg acgatatagt atgggccata     60
gataattgaa gaaataacca tctgatcaca gcttgacaca cgaatcaggt tatccatcgt    120
gtgatgacat ttttcaaaaa atatgaatgg tattaccagt ttcttgttat gctttgggtt    180
cagtaaagtt ccactcattt tccagtatct gatgaatgat agagcagtct ttttagaact    240
ttgagctttc atattccttc cgtccaacaa agatgaattt tctatggaaa aaaattgtcc    300
cacaaagata caaattttgt attttaata taaattttaa aattgttac ctgttttatc     360 ctaagtaaat aagtagataa atatttttta ttatttttaa aatatattaa aaggttaaaa    420
ttgtcagtat acattatttt ttaaaaatgt gaaatttcta taaaaaaatc catcttcata    480
ggataaagat gttattaatt ttagctatta gtcatgatca acctacactg gtacttctat    540
atttcctcca tgatatcaat ttttatgttt taaccagtga tatgaactgt gactttccac    600
cttcataact ttgatatcca tatatattag tgtaagtttc gtactgtaca tatacttgca    660
tcataactgg attagccgag actaaataat tttgactatt cttcacagtt catactcaag    720
gtctctgttc tttgtaattc tagactacat atcaaataaa aagatgatga tatattagtc    780
aaaactcaaa agtaattaga agaaaaaact ttgtaattcc ggaatatcat acgttactac    840
ttttcattag taaaatacccc aaattacttg ggaaattgag gttctgcagt tcccgatgta   900
caagagaata acaatacaat acactgatct aaagtgaatg ggacgcttga cattgccaaa    960
ccaaaccatg cttttgtatc aatatctaat aaacatataa gcttaaattt ataatgatgt   1020
attattatca aaataaacaa tgataatata acattaagat atttctagcc ttttcttttc   1080
cgcataaaag tctgtcctgg ctcattataa actaccacta atttaggcaa aatccgtatc   1140
ttaacaaaag taataaaagc aatttcgagt attgggattg gaagatacct ttccccctta   1200
ttcattcttc ttctcattct tcttttctct aaataaagta gttgagactt gagagccacc   1260
```

```
gaaaagcatt cgacatccta tcattaaagc taactttttt cagtgtttta tttctaaaat    1320
aatttcttaa aataaagaaa ggtgagagag aaattatgtc cctatacaac tagtagaatg    1380
aaagattgtc aagctttggt ttgggatttt tctaataaat cacatgcatt tgttagaatt    1440
tgatcccaaa aaaaaaaaat tcaaacctt ttcctgtaaa agcaaaccta ttggctcgta     1500
ggtcaatgtc aatctcaatg aatagtaaag tcttttgata tcacgtatct ataacatatt    1560 attttagcg tggttcatgt ccctcaacat tctgcctaaa ttataggatc tcaagacata     1620
gtactataga ctacaactac aagtagagga aaatttata agagagataa attatgcggt     1680
attcacgcat gacatgcgta agcatgaaac taaaatttgg ttgatacatt actatgccga    1740
atttaaagta gtgctccatg cagacatgaa catatcagat atcacacgta cgcatgtatt    1800
acgtgtatgt agagacacac gtacgcatat ctatattcac acaatgagat ttcactttct    1860
caaacaaaga tcactgtctt caattagttt caaatttgtt ctttacctat tgcttttaca    1920
tttctgagtg tatatattta caataaggac aaggagattt taaatgataa aagtcaacca    1980
tatcccatca tttggtcttt ggtttcccga cgtcccactt ttgtaaaaat catctgttca    2040
ttttccattc tttttctttt tcctacccaa ctggatatca ccaatgatat cattatacac    2100
taacactatc atttcacact tatcttcctc tatatataca tagcttaagt cttgtaacga    2160
gaaaggcatg catagcattt gctagtttta acatatagca                          2200
```

```
<210> SEQ ID NO 13
<211> LENGTH: 34
<212> TYPE: DNA
<213> ORGANISM: Artificial
<220> FEATURE:
<223> OTHER INFORMATION: Primer pDON_P1_pAAP6_F

<400> SEQUENCE: 13
aaaaagcagg ctgctgatgc tgttattaat ttgt                                 34

<210> SEQ ID NO 14
<211> LENGTH: 34
<212> TYPE: DNA
<213> ORGANISM: Artificial
<220> FEATURE:
<223> OTHER INFORMATION: Primer pDON_P5r_pAAP6_R

<400> SEQUENCE: 14
tatacaaagt tgctatcgat tgttttgag ctta                                  34

<210> SEQ ID NO 15
<211> LENGTH: 32
<212> TYPE: DNA
<213> ORGANISM: Artificial
<220> FEATURE:
<223> OTHER INFORMATION: Primer pDON_P1_pHYD_F

<400> SEQUENCE: 15
aaaaagcagg ctaagttagg acaacacgca aa                                   32

<210> SEQ ID NO 16
<211> LENGTH: 31
<212> TYPE: DNA
<213> ORGANISM: Artificial
<220> FEATURE:
<223> OTHER INFORMATION: Primer pDON_P5r_pHYD_R

<400> SEQUENCE: 16
tatacaaagt tgtggagatt ctcacccgca t                                    31
```

<210> SEQ ID NO 17
<211> LENGTH: 33
<212> TYPE: DNA
<213> ORGANISM: Artificial
<220> FEATURE:
<223> OTHER INFORMATION: Primer pDON_P1_pIRX3_F

<400> SEQUENCE: 17
aaaaagcagg ctcagaattc aagtagctgc cca                                   33

<210> SEQ ID NO 18
<211> LENGTH: 30
<212> TYPE: DNA
<213> ORGANISM: Artificial
<220> FEATURE:
<223> OTHER INFORMATION: Primer pDON_P5r_pIRX3_R

<400> SEQUENCE: 18
tatacaaagt tgagggacgg ccggagatta                                       30

<210> SEQ ID NO 19
<211> LENGTH: 32
<212> TYPE: DNA
<213> ORGANISM: Artificial
<220> FEATURE:
<223> OTHER INFORMATION: Primer pDON_P1_pGC1_F

<400> SEQUENCE: 19
aaaaagcagg cttttggaac actctaccaa cg                                    32

<210> SEQ ID NO 20
<211> LENGTH: 35
<212> TYPE: DNA
<213> ORGANISM: Artificial
<220> FEATURE:
<223> OTHER INFORMATION: Primer pDON_P5r_pGC1_R

<400> SEQUENCE: 20
tatacaaagt tgatttcttg agtagtgatt ttgaa                                 35

<210> SEQ ID NO 21
<211> LENGTH: 32
<212> TYPE: DNA
<213> ORGANISM: Artificial
<220> FEATURE:
<223> OTHER INFORMATION: Primer pDON_P1_WOX4_F

<400> SEQUENCE: 21
aaaaagcagg ctggcaagtg tagtggagga gg                                    32

<210> SEQ ID NO 22
<211> LENGTH: 38
<212> TYPE: DNA
<213> ORGANISM: Artificial
<220> FEATURE:
<223> OTHER INFORMATION: Primer pDON_P5r_WOX4_R

<400> SEQUENCE: 22
tatacaaagt tgtgctatat gttaaaacta gcaaatgc                              38

<210> SEQ ID NO 23
<211> LENGTH: 36
<212> TYPE: DNA
<213> ORGANISM: Artificial
<220> FEATURE:

<223> OTHER INFORMATION: Primer pDON_P1_pAHA3_F

<400> SEQUENCE: 23
aaaaagcagg ctaataacta cgtatatgct gggaag             36

<210> SEQ ID NO 24
<211> LENGTH: 34
<212> TYPE: DNA
<213> ORGANISM: Artificial
<220> FEATURE:
<223> OTHER INFORMATION: Primer pDON_P5r_pAHA3_R

<400> SEQUENCE: 24
tatacaaagt tggtggacta cgttaggcta tttg               34

<210> SEQ ID NO 25
<211> LENGTH: 32
<212> TYPE: DNA
<213> ORGANISM: Artificial
<220> FEATURE:
<223> OTHER INFORMATION: Primer pDON_P5_Kan_NcoI_F

<400> SEQUENCE: 25
atacaaaagt tgaggatgat ctggacgaag ag                 32

<210> SEQ ID NO 26
<211> LENGTH: 31
<212> TYPE: DNA
<213> ORGANISM: Artificial
<220> FEATURE:
<223> OTHER INFORMATION: Primer pDON_P2_Kan_NcoI_R

<400> SEQUENCE: 26
agaaagctgg gttgtcctga tagcggtccg c                  31

<210> SEQ ID NO 27
<211> LENGTH: 29
<212> TYPE: DNA
<213> ORGANISM: Artificial
<220> FEATURE:
<223> OTHER INFORMATION: adap_attB2

<400> SEQUENCE: 27
ggggaccact ttgtacaaga aagctgggt                     29

<210> SEQ ID NO 28
<211> LENGTH: 26
<212> TYPE: DNA
<213> ORGANISM: Artificial
<220> FEATURE:
<223> OTHER INFORMATION: adap_attB5

<400> SEQUENCE: 28
ggggacaact ttgtatacaa aagttg                        26

<210> SEQ ID NO 29
<211> LENGTH: 29
<212> TYPE: DNA
<213> ORGANISM: Artificial
<220> FEATURE:
<223> OTHER INFORMATION: adap_attB1

<400> SEQUENCE: 29
ggggacaagt ttgtacaaaa aagcaggct                     29

```
<210> SEQ ID NO 30
<211> LENGTH: 26
<212> TYPE: DNA
<213> ORGANISM: Artificial
<220> FEATURE:
<223> OTHER INFORMATION: adap_attB5r

<400> SEQUENCE: 30
ggggacaact tttgtataca aagttg                                          26

<210> SEQ ID NO 31
<211> LENGTH: 38
<212> TYPE: DNA
<213> ORGANISM: Artificial
<220> FEATURE:
<223> OTHER INFORMATION: Primer pDON_P1_pMYC1_F

<400> SEQUENCE: 31
aaaaagcagg ctgttggttc aaatcaattt tgaaatcc                             38

<210> SEQ ID NO 32
<211> LENGTH: 35
<212> TYPE: DNA
<213> ORGANISM: Artificial
<220> FEATURE:
<223> OTHER INFORMATION: Primer pDON_P5r_pMYC1_R

<400> SEQUENCE: 32
tatacaaagt tgaggagaca accaaaaggc aaaat                                35

<210> SEQ ID NO 33
<211> LENGTH: 35
<212> TYPE: DNA
<213> ORGANISM: Artificial
<220> FEATURE:
<223> OTHER INFORMATION: Primer pDON_P1_pMYB60_F

<400> SEQUENCE: 33
aaaaagcagg ctcgtgtgga gatcaacata tcttc                                35

<210> SEQ ID NO 34
<211> LENGTH: 33
<212> TYPE: DNA
<213> ORGANISM: Artificial
<220> FEATURE:
<223> OTHER INFORMATION: Primer pDON_P5r_pMYB60_R

<400> SEQUENCE: 34
tatacaaagt tgctttctct ctctctcttc ctc                                  33

<210> SEQ ID NO 35
<211> LENGTH: 37
<212> TYPE: DNA
<213> ORGANISM: Artificial
<220> FEATURE:
<223> OTHER INFORMATION: Primer pDON_P1_pCAB3_F

<400> SEQUENCE: 35
aaaaagcagg ctaaatcaag agaaaatgtg attctcg                              37

<210> SEQ ID NO 36
<211> LENGTH: 36
<212> TYPE: DNA
<213> ORGANISM: Artificial
<220> FEATURE:
<223> OTHER INFORMATION: Primer pDON_P5r_pCAB3_R
```

```
<400> SEQUENCE: 36
tatacaaagt tggattgaaa atggttaggt agggtt                              36

<210> SEQ ID NO 37
<211> LENGTH: 968
<212> TYPE: DNA
<213> ORGANISM: artificial
<220> FEATURE:
<223> OTHER INFORMATION: BDG promoter

<400> SEQUENCE: 37
gatgccacgc acacgtcctt gtcctcatga aatattacca atactactat ctatatatgg    60
atactgacag actaactctt ttaactcctg ttttaccaaa atgtgtatac atattataga   120
attgtctaaa aacaggtcag ctaggctgtt tagatgggct gctgggcatt cagagtgatg   180
gatataagtt gtggccacat gccatcatat cacttgtcca ttctttatct tatttcgcta   240
tcaacattta catttactac tctgtgccat tacttcaatt atttgatgtc tgtattagtt   300
tcactttcac ggtacgtaat cacatttgta tccatagccc aaaaaaaaaa cacatttata   360
tccatatagt ttagttgccc tccttgtagt tttagacccc aaaagtcatc aaccggccaa   420
aatcctcaat agtggcctta ccaaacagag catatatgag tatcattaat tattgggact   480
atctagggtt ttgattgttt tcaaatacaa aattacatgc cttcttagca tattattttc   540
acattattaa acataatttc ttgtaaccct aaggaaggaa ccgcacatcc ataatgactt   600
gactgacttt gtgtgtatgt agctatagcg gcattttgga tcatcaccgg accaatcgac   660
atcacatgtt ccttagtatt gattcctgtt ttgaagttaa aaaagatatt acggtatgtg   720
ctggatatgc gtggtctagt gttgcaaaaa aaaaggaaga agattcaacg gccaccaaat   780
ttcatcattt tagccaacaa tgtatgttaa atgcgatcaa taaattcatg cagctgccat   840
ctgttttcct ctctctcttc attaacttaa tttctctctc tcacgcattt tgtctttgca   900
acatcaccac catacataca tacaacttac atacatacac gtcttccaca agactcaaac   960
tccacagc                                                           968

<210> SEQ ID NO 38
<211> LENGTH: 30
<212> TYPE: DNA
<213> ORGANISM: Artificial
<220> FEATURE:
<223> OTHER INFORMATION: primer pDON_P1_pBDG_F

<400> SEQUENCE: 38
aaaaagcagg ctgatgccac gcacacgtcc                                    30

<210> SEQ ID NO 39
<211> LENGTH: 33
<212> TYPE: DNA
<213> ORGANISM: Artificial
<220> FEATURE:
<223> OTHER INFORMATION: primer pDON_P5r_pBDG_R

<400> SEQUENCE: 39
tatacaaagt tggctgtgga gtttgagtct tgt                                33
```